(12) United States Patent
Abbott et al.

(10) Patent No.: US 9,080,973 B2
(45) Date of Patent: Jul. 14, 2015

(54) ANALYTE DETECTION USING LIQUID CRYSTALS

(75) Inventors: Nicholas L. Abbott, Madison, WI (US); I-Hsin Lin, Manchester (GB); Christopher J. Murphy, Davis, CA (US); Jugal Gupta, Houston, TX (US)

(73) Assignee: Wisconsin Alumni Research Foundation, Madison, WI (US)

( * ) Notice: Subject to any disclaimer, the term of this patent is extended or adjusted under 35 U.S.C. 154(b) by 495 days.

(21) Appl. No.: 12/765,695

(22) Filed: Apr. 22, 2010

(65) Prior Publication Data

US 2011/0007261 A1 Jan. 13, 2011

Related U.S. Application Data

(60) Provisional application No. 61/171,699, filed on Apr. 22, 2009, provisional application No. 61/324,650, filed on Apr. 15, 2010.

(51) Int. Cl.

| | | |
|---|---|---|
| G01N 21/77 | (2006.01) | |
| G01N 21/85 | (2006.01) | |
| G01N 21/88 | (2006.01) | |
| G01N 31/22 | (2006.01) | |
| G01N 33/52 | (2006.01) | |
| G01N 21/51 | (2006.01) | |
| G01N 21/21 | (2006.01) | |
| G01N 21/64 | (2006.01) | |
| G01N 21/47 | (2006.01) | |

(52) U.S. Cl.
CPC .............. *G01N 21/51* (2013.01); *G01N 21/21* (2013.01); *G01N 21/6428* (2013.01); *G01N 21/77* (2013.01); *G01N 2021/4704* (2013.01)

(58) Field of Classification Search
None
See application file for complete search history.

(56) References Cited

U.S. PATENT DOCUMENTS

| 6,284,197 | B1 | 9/2001 | Abbott et al. | |
|---|---|---|---|---|
| 6,288,392 | B1 | 9/2001 | Abbott et al. | |
| 7,267,956 | B2 * | 9/2007 | Harvey et al. | 435/6.14 |
| 2005/0064395 | A1 * | 3/2005 | Israel et al. | 435/5 |
| 2007/0004046 | A1 * | 1/2007 | Abbott | 436/104 |
| 2009/0023155 | A1 | 1/2009 | Abbott | |

FOREIGN PATENT DOCUMENTS

WO WO9963329 12/1999

OTHER PUBLICATIONS

Brake, Jeffrey M., et al., Biomolecular Interactions at Phospholipid-Decorated Surfaces of Liquid Crystals, Science, 2003, 302, 2094-2097.

Gupta, Jugal K., et al., Size-Dependent Ordering of Liquid Crystals Observed in Polymeric Capsules with Micrometer and Smaller Diameters, Angew. Chem. Int. Ed., 2009, 48, 1652-1655.

(Continued)

*Primary Examiner* — Brian R Gordon
(74) *Attorney, Agent, or Firm* — Quarles & Brady LLP

(57) ABSTRACT

Devices and methods for using changes in the defects in micrometer sized dispersed liquid crystal domains to detect or quantify analytes in a test sample, including endotoxin lipopolysaccharide (LPS), are disclosed. The dispersed liquid crystal microdomains are exposed to the test sample, and any changes in the number of defects in the liquid crystal microdomains are detected by detecting changes in the anchoring configuration of the microdomains. Such changes in anchoring configuration indicate the presence of analyte in the test sample.

33 Claims, 19 Drawing Sheets

(56) References Cited

OTHER PUBLICATIONS

Heppenstall-Butler, M., et al., Selection of Droplet Size and the Stability of Nematic Emulsions, Liquid Crystals, 2005, 32(1), 77-84.

McCamley, Maureen K., et al., Optical Detection of Sepsis Markers Using Liquid Crystal Based Biosensors, Proc. of SPIE, 2007, 6441, 64411Y-1-64411Y-8.

Poulin, Philippe, et al., Novel Colloidal Interactions in Anisotropic Fluids, Science, 1997, 275, 1770-1773.

Lockwood, et al., "Self-assembly of amphiphiles, polymers and proteins at interfaces between thermotropic liquid crystals and aqueous phases" 2008 Surface Science Reports, Elsevier Science, vol. 63, No. 6, pp. 255-293.

Tjipto, et al., "Tailoring the Interfaces between Nematic Liquid Crystal Emulsions and Aqueous Phases via Layer-by-Layer Assembly" 2006 Nano Letters, vol. 6, No. 10, pp. 2243-2248.

Brake, et al., "Coupling of the orientations of thermotropic liquid crystals to protein binding events at lipid-decorated interfaces" 2007 Langmuir vol. 23, No. 16, pp. 8497-8507.

Hsu P et al: "Rotational diffusion of Monodisperse Liquid Crystal Droplets" 1998 Journal of Colloid and Interface Science, vol. 200, pp. 182-184.

International Search Report issued in PCT/US2010/032055 mailed Aug. 24, 2010.

\* cited by examiner

ANALYTE DETECTION USING LIQUID CRYSTALS

CROSS-REFERENCE TO RELATED APPLICATION

This application claims the benefit of U.S. Provisional Patent Application No. 61/171,699, filed on Apr. 22, 2009, and U.S. Provisional Patent Application No. 61/324,650, filed on Apr. 15, 2010, which are incorporated by reference herein in their entirety.

STATEMENT REGARDING FEDERALLY SPONSORED RESEARCH OR DEVELOPMENT

This invention was made with government support under 0520527 and 0602570 awarded by the National Science Foundation. The government has certain rights in the invention.

FIELD OF THE INVENTION

This invention relates generally to methods of analyte detection using liquid crystals. In particular, the present invention is directed to systems and methods utilizing micrometer-sized domains of liquid crystals to detect analytes such as endotoxin lipopolysaccharide (LPS) in an aqueous solution.

BACKGROUND OF THE INVENTION

The detection and quantification of endotoxin (lipopolysaccharide, LPS) is critically important in a wide range of health-related contexts, including human healthcare, clinical and basic medical research, pharmaceutical manufacturing, occupational and public health and food and water purity testing. Currently, most endotoxin detection or quantification methods are based on the Limulus Amoebocyte Lysate-related gelation reaction or chromogenic response as modified from the original Limulus Amoebocyte Lysate Assay (LAL Assay) first reported in 1960s.

The Limulus Amoebocyte is the only circulating cell found in the blood of *Limulus polyphemus*, the horseshoe crab. When a horseshoe crab acquires a Gram-negative bacterial infection, the Limulus Amoebocyte Lysate enzyme interacts with the Lipid A portion of the LPS produced and triggers extracellular coagulation. This reaction is the basis of a number of assay methods used for detecting and quantifying endotoxin in aqueous specimens (e.g., kinetic turbidimetric LAL assay, kinetic chromogenic LAL assay, Gel-Clot LAL, and End-Point LAL), and endotoxin detection limits using these assays can be as low as the pg/mL range.

However, the current LAL-based assays have a number of disadvantages. For example, LPS isolated from different species of bacteria do not activate LAL equally. In addition, certain substances interfere with LAL's ability to react with endotoxin. Furthermore, since the lysate is a crude and variable mixture, not a single purified enzyme, the enzyme activity needs to be standardized for every batch of LAL extracted using a complex and expensive procedure. The reagents for LAL assays are also derived from animals, and the reagents need to be stored under controlled conditions, such as controlled temperature. In general, the complexity of the assays requires the use of skilled technicians. The limitations of current assays for LPS demonstrate a continuing need for a simple and low cost, yet rapid, sensitive and selective, assay for reporting and quantifying LPS in aqueous samples.

Previously, assay devices that employ liquid crystals as a means to detect and quantify various analytes have been disclosed. For example, a liquid crystal assay device using mixed self-assembled monolayers (SAMs) containing octanethiol and biotin supported on an anisotropic gold film obliquely deposited on glass has been reported. Gupta, V. K.; Skaife, J. J.; Dubrovsky, T. B., Abbott N. L. Science, 279, (1998), pp. 2077-2079. In addition, PCT publication WO 99/63329 published on Dec. 9, 1999, discloses assay devices using SAMs attached to a substrate and a liquid crystal layer that is anchored by the SAM. U.S. Pat. No. 6,288,392 issued to Abbott et al. discloses the quantitative characterization of obliquely-deposited substrates of gold using atomic force microscopy and describes the influence of substrate topography on the anchoring of liquid crystals. U.S. Pat. No. 6,284,197 issued to Abbott et al. discloses the optical amplification of molecular interactions using liquid crystals.

Past studies have also reported on the influence of surfactants on the orientations of liquid crystals when the surfactants are adsorbed at interfaces of aqueous phases and thermotropic liquid crystals in emulsions (Drzaic, Liquid Crystal Dispersions. Series on Liquid Crystals; World Scientific: Singapore, 1995; Poulin et al. Science 1997, 275, 1770; Mondain-Monval et al. Eur. Phys. J B 1999, 12, 167). More recently, planar interfaces between thermotropic liquid crystals and aqueous solutions have been used to investigate the orientations of liquid crystals decorated with surfactants (Brake et al. Langmuir 2002, 16, 6101; Brake et al. Langmuir 2003, 16, 6436; Brake et al. Langmuir 2003, 21, 8629), lipids (Brake et al. Science 2003, 302, 2094; Brake et al. Langmuir 2005, 21, 2218), and proteins (Brake et al. Science 2003, 302, 2094). Most recently, the use of a sensor made of multiple grids filled with liquid crystal to detect varying concentrations of LPS in a test sample has been discussed, although the structure of the molecule shown in the paper to be the subject of this study is not LPS nor is it lipid A (McCamley et al. Proc. SPIE 2007, 6441, 64411Y).

There remains a continuing need in the art for new assays for detecting and quantifying LPS at low limits of detection that are specific to LPS and faster than previously disclosed methods.

SUMMARY OF THE INVENTION

Surprisingly, the inventors have discovered that anchoring configuration transitions in micrometer-sized droplets of liquid crystal dispersed in aqueous solution are observed in the presence of <1 pg/ml concentrations of lipid A or LPS endotoxin. In addition, the inventors have determined that by observing such anchoring configuration transitions, endotoxin in the 0.1-1000 pg/mL range can be quantified within one minute, much faster than can be done with presently available LPS assays. This sensitivity is far greater than that which is achieved through the adsorption of lipids over the interface of planar films of liquid crystal as reported by McCamley et al or Brake et al.

Although the invention is not limited by any proposed theory or mechanism of action, the bacterial lipid apparently triggers the anchoring configuration transitions by changing the energies of topological point defects that are generated by using liquid crystal droplets, rather than by uniform adsorption over the aqueous interface of the liquid crystal droplet. This newly discovered mechanism for driving anchoring configuration transitions is exquisitely sensitive to the specific lipidic architecture of endotoxin.

Accordingly, in a first aspect, the invention encompasses a liquid crystal-based sensor for detecting an analyte in a test sample. The sensor includes one or more liquid crystal microdomains that are confined by an interface that generates one or more defects in the liquid crystal microdomains, as well as a detector capable of characterizing the orientational order of the liquid crystal microdomains. A preferred liquid crystal making up the microdomains is 4'-pentyl-4-cyanobiphenyl (5CB).

In certain embodiments, the microdomains are confined within droplets, within microwells, within capillaries, on surfaces, or within another material. Preferably, the microdomains have curved interfaces.

Preferably, the liquid crystal microdomains are dispersed and have a minor axis of between about 0.5 μm and about 200 μm. More preferably, the microdomains have a minor axis of between about 1 μm and about 10 μm, and most preferably, the microdomains have a minor axis of between about 2 μm and about 4 μm.

In some embodiments, the sensor includes a plurality of liquid crystal microdomains dispersed within a material that is supported on a solid support. In certain embodiments, the microdomains are dispersed liquid crystal droplets within a liquid crystal emulsion. In some such embodiments, the liquid crystal emulsion may contain an LPS free aqueous phase. The LPS free aqueous phase may optionally include an LPS free buffer, such as phosphate buffered saline (PBS).

In certain embodiments, the sensor also includes an aqueous test sample in contact with the liquid crystal emulsion. Preferably, the volume ratio of the aqueous test sample to the liquid crystal contained within the liquid crystal emulsion is greater than or equal to about 100 to 1; more preferably, the ratio is greater than or equal to about 1,000 to 1; most preferably, the ratio is greater than or equal to about 40,000 to 1.

Preferably, the detector included in the sensor characterizes the orientational order by determining the number of defects in the liquid crystal microdomains, detecting the anchoring configuration of the microdomains, or both. The detector optionally uses light-based detection, and may be a light-based imaging device, including without limitation a polarized light-based imaging device, a fluorescence-based imaging device, a detector that detects scattered, or a detector that detects transmitted light. The sensor may further include a bright field light source. In certain embodiments, the detector is located on a flow device, including without limitation a flow cytometer. Optionally, the flow cytometer uses a fluorescence-based mode of detection.

In certain preferred embodiments, at least one of the liquid crystal microdomains included in the device has two point defects. The sensor may optionally include an analyte in contact with the microdomains, preferably where at least one of the microdomains has one point defect. In some such embodiments, the analyte is partitioned to the defects in the microdomains. A preferred analyte is endotoxin lipopolysaccharide (LPS) or lipid A.

In certain embodiments, the liquid crystal microdomains are immobilized. In some such embodiments, the microdomains contain a polymer adsorbed to the surface of the microdomains, and the polymer facilitates the immobilization of the microdomains on a substrate surface. Alternatively, the microdomains are immobilized within a hydrophilic polymer network, within a gel formed from colloids or polymers, or within a dehydrated material. Optionally, an absorbent material is placed in contact with the material within which the liquid crystal microdomains are immobilized.

The sensor of the invention further encompasses a liquid crystal-based sensor for detecting endotoxin lipopolysaccharide (LPS) in a test sample. Such a detector includes a material containing dispersed liquid crystal microdomains having a minor axis of between about 0.5 μm and about 200 μm, and a detector capable of detecting the anchoring configuration of the liquid crystal microdomains.

In a second aspect, the invention encompasses a method for detecting an analyte in a test sample. The method includes the steps of (a) providing one or more liquid crystal microdomains having one or more defects; contacting the microdomains with a test sample; and (c) using a detector to determine the orientational order in the liquid crystal microdomains by, for example, detecting the number of defects in the microdomains. A change in the number of defects indicates the presence of the analyte in the test sample. Preferably, the interface of the liquid crystal microdomain is curved.

In some embodiments, the change in the number of defects in the liquid crystal microdomains is a reduction in the number of defects within the microdomains, as, for example, a change from two defects to one defect. The number of defects in the liquid crystal microdomains may be directly detected, or may be determined by detecting the anchoring configuration of the microdomains.

Preferably, the liquid crystal microdomains have a minor axis of between about 0.5 μm and about 200 μm; more preferably, the liquid crystal microdomains have a minor axis of between about 1 μm and about 10 μm; and most preferably, the liquid crystal microdomains have a minor axis of between about 2 μm and about 4 μm. In certain embodiments, the test sample is an aqueous test sample. Preferred analytes for detecting using the method include endotoxin lipopolysaccharide (LPS) and lipid A.

Preferably, the step of using a detector to detect any change in configuration of the liquid crystal microdomains is performed by one or more of optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, or using a cuvette in a detector. Optionally, a microfluidic device and/or a solid support may be used to deliver the sample to the detector. Preferably, all pipettes, plasticware, vessels, and other devices used in performing the method are LPS free.

In certain embodiments, a plurality of dispersed liquid crystal microdomains are provided. In some such embodiments, the liquid crystal defect information obtained for the dispersed microdomains may further be used to quantify the analyte present in the sample. Preferred analytes for quantification using the method include endotoxin lipopolysaccharide (LPS) or lipid A. In other embodiments, the liquid crystal defect information obtained for the dispersed microdomains may further be used to differentiate LPS or Lipid A from other lipids.

In certain embodiments, the dispersed liquid crystal microdomains are provided in a water emulsion, and the liquid crystal microdomains are liquid crystal droplets within the emulsion. Preferably, the emulsion is LPS free, and may contain an LPS free buffer.

The test sample may be an aqueous test sample. In such embodiments, the volume ratio of the aqueous test sample to the liquid crystal contained within the liquid crystal emulsion is preferably greater than or equal to about 100 to 1; more preferably greater than or equal to about 1,000 to 1; and most preferably greater than or equal to about 40,000 to 1.

The method of detecting analyte further encompasses a method for detecting endotoxin lipopolysaccharide (LPS) in a test sample. Such a method includes the steps of (a) providing a material comprising dispersed liquid crystal microdomains having a minor axis of between about 0.5 μm and about 200 μm; (b) contacting the material with an aqueous test sample; and (c) using a detector to detect the anchoring configuration of the liquid crystal microdomains.

In a third aspect, the invention encompasses a method of making a liquid crystal-based sensor for detecting an analyte in a test sample. The method includes the steps of (a) providing a material including dispersed liquid crystal microdomains having a minor axis of between about 0.5 μm and about 200 μm; and (b) providing a detector capable of detecting the anchoring configuration of the liquid crystal microdomains. Preferably, the material including the dispersed liquid crystal microdomains is a liquid crystal emulsion, and the step of providing the emulsion further comprises the steps of sonicating and vortexing a mixture containing liquid crystal and LPS free buffer. In some such embodiments, the steps of sonicating and vortexing the mixture are performed multiple times on the same mixture.

The step of providing the material comprising dispersed liquid crystal microdomains may further include forming a hydrogel about the dispersed liquid crystal microdomains, or using other methods to immobilize the dispersed liquid crystal microdomains onto a substrate surface.

Other objects, features and advantages of the present invention will become apparent after review of the specification, claims and drawings.

BRIEF DESCRIPTION OF THE DRAWINGS

FIG. 4A is an optical image and FIG. 4D is a cartoon representation showing 5CB anchoring upon contact with PBS buffer solution. FIG. 4B is an optical image and FIG. 4E is a cartoon representation showing 5CB anchoring upon contact with 2 mL of 1 microgram/mL LPS in PBS buffer for 24 hours at 25° C. FIG. 4C is an optical image and FIG. 4F is a cartoon representation showing 5CB anchoring upon contact with 2 mL of 1 milligrams/mL LPS in PBS buffer for less than two minute at 25° C. The inset of FIG. 4C is an interference pattern obtained by conoscopic imaging of 5CB. Scale bars are 300 um.

DETAILED DESCRIPTION OF THE INVENTION

I. IN GENERAL

Figure 1:
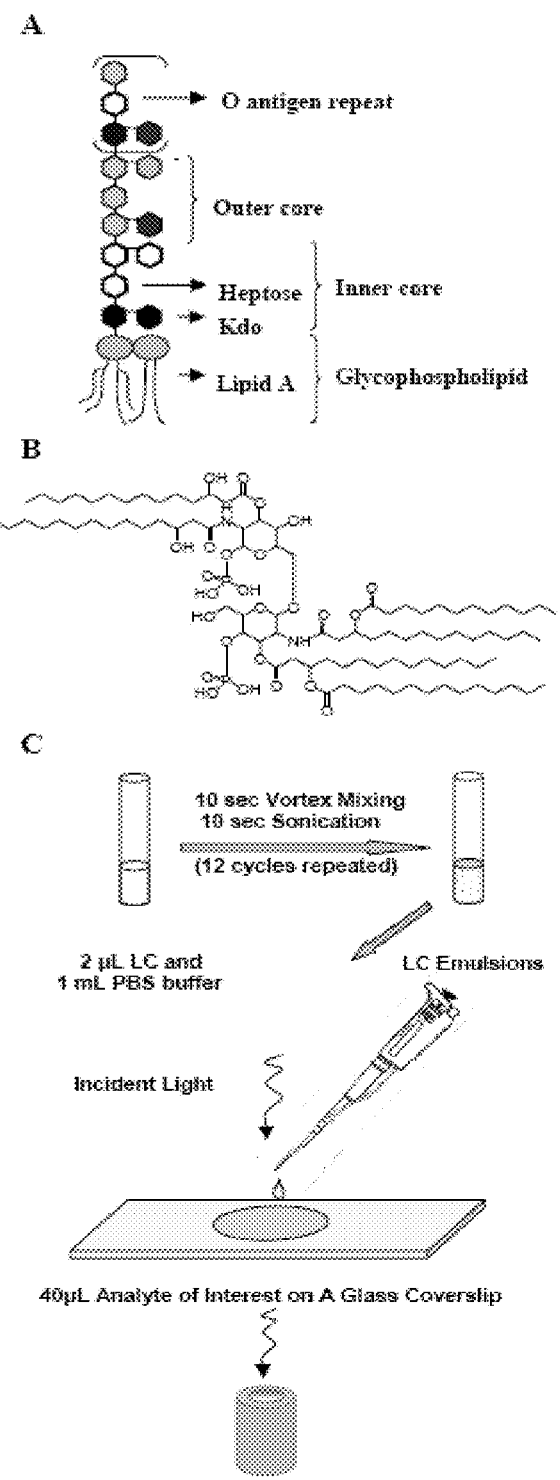
FIG. 1A shows a schematic representation of bacterial lipopolysaccharide (LPS), an endotoxin found in the outer membrane of Gram-negative bacteria.
FIG. 1B shows the molecular structure of lipid A, the biphosphorylated lipid component of LPS.
FIG. 1C is a schematic representation of the protocol used to prepare LC emulsions and the experimental setup used to visualize microscopically the LC emulsion anchoring transition occurring upon contact with an analyte of interest.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention.

As used herein and in the appended claims, the singular forms "a", "an", and "the" include the plural forms unless the context clearly dictates otherwise. As well, the terms "a" (or "an"), "one or more" and "at least one" can be used interchangeably, and the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, "liquid crystal" means an organic composition in an intermediate or mesomorphic state between solid and liquid. Suitable liquid crystals for use in the present invention include, but are not limited to, thermotropic, polymeric, lyotropic, chromonic, smectic, nematic, ferroelectric and cholesteric liquid crystals.

A "microdomain" of liquid crystal refers to a volume of material in the liquid crystal phase defined by an interface wherein the volume has a minor axis that is not at any point larger than 200 µm across and the minor axis is defined as the shortest length across the volume of the liquid crystal.

The term "anchoring configuration" of the microdomain is used herein to describe the ordering of the liquid crystal within the microdomain, and is not used to imply the mechanism that leads to the ordering. In particular, it is not used to imply that the ordering results from the uniform adsorption of the analyte over the interface of the liquid crystal microdomain. Indeed, a unique aspect of the current invention is that the LPS is reported without uniform adsorption over the surface of the liquid crystal microdomain, thus distinguishing this invention from prior art.

The term "defect" as used herein means a local region in a liquid crystal where the orientational order of the molecules in the liquid crystal is different from the surrounding region, as described in text books such as "The Physics of Liquid Crystals" by P. G. de Gennes. The core of a defect is typically nanoscopic in size, and scatters light. Locally, within the cores of most defects, the orientational order of the liquid crystal is low compared to the surrounding region. Defects can be lines (typically called disclination lines) or points in a liquid crystal, as well as other geometries (see text referenced above).

"LPS," also referred to interchangeably herein as "lipopolysaccharide" or "endotoxin," means a lipopolysaccharide comprised of a hydrophobic glycophospholipid region, called lipid A (see FIG. 1B for detailed structure), and two polysaccharide portions (called the core polysaccharide chain and O-antigenic polysaccharide side chain) (see FIG. 1A). LPS is heterogeneous and strongly self-associating, with molecular weights ranging from 10-20 KDa. LPS is a constituent of the outer membrane of Gram-negative bacteria, and is released to the environment upon bacterial proliferation or death. The term LPS is used herein to include fragments of LPS such as a the lipid A component of LPS.

Lipid A serves as a hydrophobic anchor of the LPS to the outer membrane of the Gram-negative bacteria. The minimal LPS structure required for the bacterial growth consists of lipid A and Kdo (3-deoxy-D-manno-oct-2-ulosonic acid) domain (see FIG. 1A), although in wild-type bacterial strains, core polysaccharide chains and O-antigenic polysaccharide side chains may present. The lipid A architecture has been shown to be largely conserved between various Gram-negative bacterial strains, and both the self-associating tendency of the LPS and the capability of LPS to bind to host cell membranes is attributed to the lipid A component of the molecule. Variations in the structure of lipid A between bacteria can include the presence of 7 hydrophobic tails, rather than the 6 shown in FIG. 1B. The scope of the invention covers these variations in the structure of lipid A, and it is not restricted to the structures shown in FIG. 1.

The core polysaccharide region of the LPS mainly (see FIG. 1A) consists of heptose resides (which often are substituted by phosphate, pyrophosphate, or diphosphoethanolamine) in the "inner core" polysaccharide chains (lipid A proximal) and sugar components (D-glucose, D-galactose, D-glucosamine, D-galactosamine, or N-acetyl derivatives) in the "outer core" (O-antigen proximal). The repeating units of the "O-antigenic polysaccharide chain" consist of 1 to 8 sugars, with the entire chain containing up to 50 units.

"LPS free" means a medium that contains a concentration of LPS that is well below the concentration range of interest. For example, if the concentration range of LPS of interest in a sample is 100 pg/ml to 1000 pg/ml of LPS, then a buffer containing less than 0.1 pg/ml of LPS would be considered LPS free. Many buffers are commercially available that are sold as "LPS free". Some of these "LPS free" buffers are validated to contain less than 2 pg/ml of LPS. Such buffers are useful for dilution of samples that may contain concentration of LPS that are much greater than 2 pg/ml.

The following abbreviations are used throughout the present disclosure: LC, liquid crystal; LAL, Limulus Amoebocyte Lysate; PBS, phosphate buffered saline; LPS, lipopolysaccharide; 5CB, 4'-pentyl-4-cyanobiphenyl; LOD, limit of detection; OTS, Octadecyltrichlorosilane; DLPC, dilauroylphosphatidylcholine; SDS, sodium dodecylsulfate; DOPC, dioleoylphosphatidylcholine; BODIPY FL, the fluorophore 4,4-difluoro-4-bora-3a,4a-diaza-s-indacene (BODIPY®FL, Life Technologies, Carlsbad, Calif.).

II. THE INVENTION

Although the invention is not limited by any proposed theory or mechanism of action, the inventors have demonstrated that certain analytes, including without limitation LPS and lipid A, trigger anchoring configuration transitions on contact with liquid crystal microdomains by changing the energies of topological point defects that are generated within such liquid crystal microdomains, rather than by the previously recognized mechanism of uniform adsorption over the aqueous interface of the liquid crystal microdomain. This newly discovered mechanism for driving anchoring configuration transitions is exquisitely sensitive to the specific architecture of the analyte, providing the basis for extraordinarily sensitive sensors and methods for detecting certain analytes.

In particular, the inventors have recently determined that contacting LPS with micrometer-sized domains of LC (microdomains) can trigger changes in the anchoring configuration of the LCs within the domains. In a particular embodiment of the invention, the domains of LC comprise LC droplets dispersed in an aqueous phase. The anchoring configurations of the LC domains and droplets (including the changes induced by LPS) can be determined in a low resource environment by visual inspection using polarized or bright field microscopy, or in a high through-put environment by using a continuous flow device such as a flow cytometer. Measurements of electrical capacitance can also be used to determine the configuration of the liquid crystal within the microdomains.

Other methods of detection of the configurations of LCs within micrometer-sized domains and droplets are well known to those skilled in the art, including the use of fluorescent probes and dichroic dyes to report the ordering of the LC. The inventors have also observed that the radial configuration of LC droplet can serve as a light wave guide, leading to fluorescent signatures of the LC droplets that permit distinction between radial and bipolar configurations. This discovery indicates that fluorescence intensity measurements and fluorescence microscopy can also be used to report the ordering of the LC in the micrometer sized domains. For example, many flow devices can report the fluorescent signature of micrometer-sized objects, including devices such as flow cytometers.

Accordingly, the present invention provides devices and methods for detecting an analyte in a test sample by determining the configuration of one or more LC microdomains after exposing the LC microdomains to the test sample. In this patent application we define the term droplet of LC to be a microdomain of LC, but the LC microdomains of the invention are not limited to only droplets of LC dispersed in aqueous solutions. Instead, the invention includes composite materials containing microdomains of LC, such as polymeric and inorganic materials. The microdomain of LC may be either mobile or immobile, and the scope of this invention covers both immobile and mobile droplets. In addition, the shape of the domain is not limited to a spherical shape. Shapes other than spherical, including hemispherical shapes formed by droplets on surfaces, are covered within the scope of this invention.

As one skilled in the art would recognize, the device and methods of the present invention would have many uses, including without limitation monitoring a water supply in a laboratory or manufacturing plant for LPS, measuring LPS in serum, measuring LPS in aerosols, monitoring levels of LPS in a work place, monitoring LPS in a patient, determining LPS levels in water to be used for injection or inhalation, or preparation of a therapeutic compound. It could also be used for determining LPS in a rural clinic or in foods. It could also be used for measuring LPS in situations where compounds that interfere with the LAL assay are present. It could also be used where high levels of automation are desired, the cost of the LAL assay is prohibitive, or where rapid analysis (less than 15 mins to one hour) is needed.

The feasibility of the approach has been established in the following examples, which show that the LC-based methods of the present invention can detect LPS in a test sample with more sensitivity (LOD 0.1-1 pg/mL) and faster (within one minute) than is possible using conventional LAL assays, without the need for biological reagents. At concentrations below 1 µg/ml of lipid in solution, the detection response of the LC droplets using the present method is specific to LPS, and the method does not detect phospholipids such as DLPC and DOPC or other synthetic surfactants at such concentrations. In addition, in contrast to LAL assays, different LPS bacterial strains (from $E.\ coli$ O127:B8 and $E.\ coli$ O111:B4) can be detected with comparable sensitivities by using the LC-based droplets of the present invention. Furthermore, when using liquid crystal emulsions of the present invention, the volume ratio of test sample to liquid crystal emulsion can be tuned to maximize the sensitivity (LOD) of the LPS detection method. Finally, quantification of the configurations of the LC within the LC domains used in the present invention offers approaches to the quantification of LPS or other analyte concentration in the test sample.

In the examples below, the liquid crystal used is 4-cyano-4'-pentylbipheny-1 (5 CB) (see FIG. 2A). The assembly of these molecules into a so-called nematic LC phase is illustrated in FIG. 2B, where the molecules exhibit long-range orientational order that is not found in isotropic liquids. As the LC of the present invention are essentially ordered oils, emulsions containing droplets of nematic phase LC dispersed in aqueous phases can be created, or domains of LC can be contacted with aqueous phases without dissolution of the LC into the aqueous phase. A large number of methods can be used to create the LC dispersed phase, including sonication of LC in an aqueous phase, extrusion through a membrane, mechanical agitation, flow focusing, including flow focusing in microfluidic channels. FIG. 2C shows an optical image of emulsion droplets of LC prepared in aqueous buffer.

Within these droplets of LC, the organization of the LC, known as the "anchoring configuration," depends both on the state of the interface between the LC and aqueous phase and the thermodynamics associated with the one or more point defects characteristic of the given anchoring configuration. Depending on the size of the droplets, the structure, concentration and organization of any interfacial adsorbates, and the association of such adsorbates with any point defects present within the droplets, the anchoring configuration of the LC within the droplets can vary substantially, and this variation can be detected using optical and other detection methods. See Gupta et al. Angew. Chem. Int. Ed. 2008, 48, 1652-55. The configuration of the LC is dictated by the interfacial interactions of the LC as well as the energy stored in the volume of the LC droplets as a consequence of elastic strain of the LC.

Figure 2:
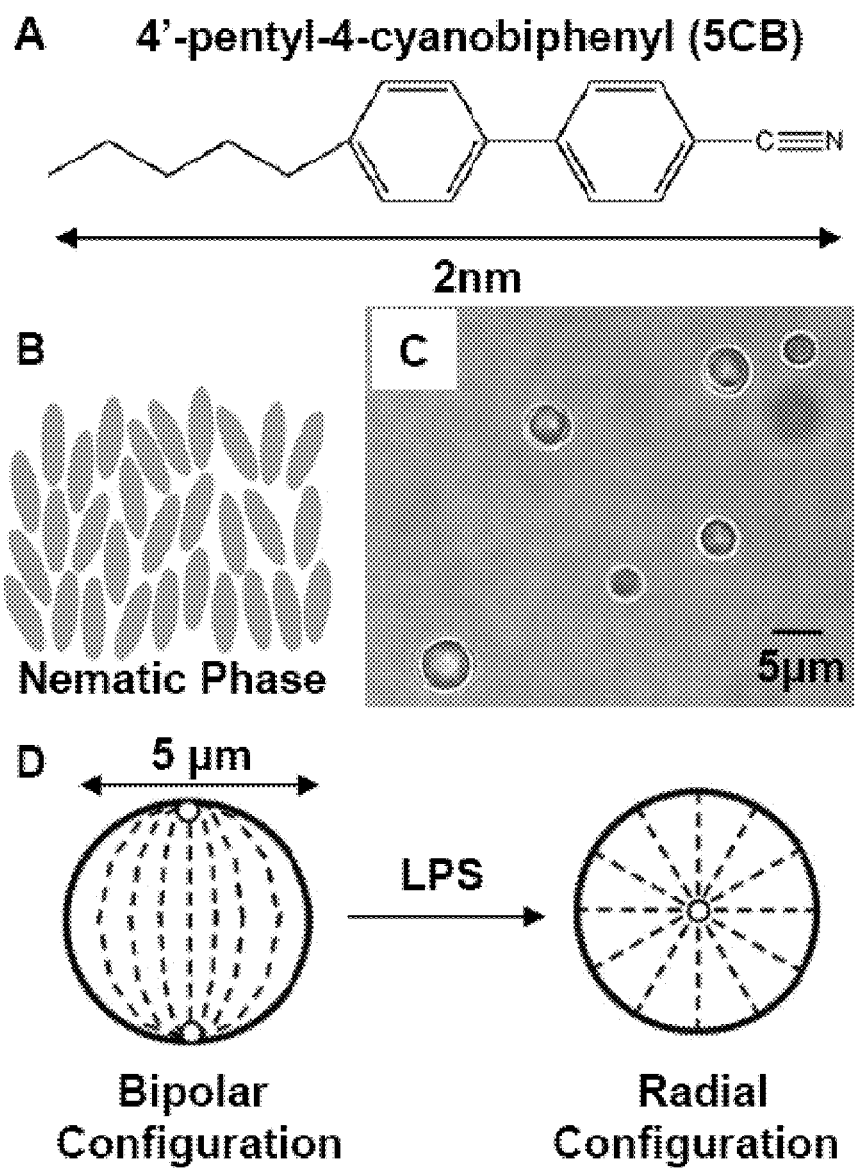
FIG. 2A shows the molecular structure of 5CB, one molecule that forms LC.
FIG. 2B is a schematic illustration of the organization of molecules in a nematic LC.
FIG. 2C is an optical micrograph of droplets of nematic LC dispersed in aqueous buffer.
FIG. 2D is a schematic illustration of the change in structure of the LC droplets upon contact with LPS. Before contacting the LPS, the LC in the droplet assumes a bipolar configuration, and after contacting the LPS, the LC in the droplet assumes a radial configuration.

FIG. 2D illustrates the two anchoring configurations of the LC droplets that are seen in the present invention. When the LC within the droplets anchor to the internal interface of the droplets with a tangential orientation, the anchoring configuration of the LC corresponds to a so-called "bipolar configuration" (FIG. 2D left side). In contrast, if the LC anchors with an orientation that is perpendicular to the interface, the configuration of the LC droplet changes to a "radial configuration" (FIG. 2D right side).

Surprisingly, the inventors have shown that contacting LPS with μm size LC droplets at the LC droplet interface can trigger the LC droplets to change very quickly from the "bipolar" to the "radial" configuration at remarkably low LPS concentrations, and with a specificity that is high relative to other compounds commonly present in biological matrices (i.e. salts, other lipids, proteins, nucleic acids). The low concentration of LPS required to trigger the anchoring configuration transition within the LC droplets as compared to the concentration of other lipids required to trigger the anchoring configuration transition can be explained if the endotoxin triggers the anchoring configuration transition through interaction with a localized region of the LC droplet, such as one or more point defects, and not through uniform surface adsorption, as has been established for other lipids. This newly-discovered mechanism is further demonstrated in the examples.

In a first aspect, the invention encompasses a liquid crystal-based sensor for detecting an analyte in a test sample. The analyte is preferably but not limited to LPS or lipid A. The sensor includes one or more liquid crystal microdomains and a detector capable of detecting the anchoring configuration of or the number of defects within the liquid crystal microdomains. Preferably, the microdomains are dispersed and have a minor axis of between about 0.5 μm and about 200 μm. More preferably, the liquid crystal microdomains have a minor axis of between about 1 μm and about 10 μm, and most preferably, the liquid crystal microdomains have a minor axis of between about 2 μm and about 4 μm. Although a variety of liquid crystals may be used in the invention, a preferred liquid crystal is 4'-pentyl-4-cyanobiphenyl (5CB).

In some preferred embodiments, the liquid crystal microdomains possess topological defects prior to exposure of the liquid crystal microdomains to the analyte. In a preferred embodiment the liquid crystal microdomains possess two or more surface point defects prior to interaction with the analyte, and fewer point defect after interaction with the analyte to report the presence of the analyte. In a preferred embodiment, the two or more point defects in the initiate state of the liquid crystal are generated by confinement of the liquid crystal in non-planar geometries, including droplets, surface-supported droplets, microwells without limitation on the shapes of the microwells, and capillaries. The two of more defects can also be generated by the dispersing of solid objects in the liquid crystal, including colloidal particles which are well known to lead to the generation of topological defects in liquid crystals. A key aspect of the invention is that the interaction of the analyte such as LPS with the defective liquid crystal microdomain results in a reduction in the number of defects within the liquid crystal.

Preferably, the number of defects in a liquid crystal microdomain may be determined by detecting the anchoring configuration of the liquid crystal within the microdomain. In a preferred embodiment, the two or more defects are generated in the liquid crystal by using liquid crystal microdroplets with two surface defects called Boojums in the bipolar configuration. The presence of the analyte is reported by a transition in the microdroplet configuration to a radial configuration where the single point defect at the center of the microdomain is stabilized by the analyte.

In some preferred embodiments, the liquid crystal microdomains are liquid crystal droplets dispersed in a liquid crystal emulsion. In some such embodiments, the liquid crystal emulsion is a liquid crystal in water emulsion where the aqueous phase is LPS free. In some embodiments, the aqueous phase of the emulsion may include a buffer to control the pH. A non-limiting example of an appropriate LPS free buffer for use in such an embodiment is phosphate buffered saline (PBS).

In further embodiments, the liquid crystal-based sensor additionally includes an aqueous test sample in contact with the liquid crystal emulsion. In such embodiments, a preferred volume ratio of the aqueous test sample to the liquid crystal contained within the liquid crystal emulsion is greater than or equal to about 100 to 1, with a more preferred volume ratio of the aqueous test sample to the liquid crystal contained within the liquid crystal emulsion of greater than or equal to about 1,000 to 1, and a most preferred volume ratio of the aqueous sample to the liquid crystal contained within the liquid crystal emulsion of greater than or equal to about 40,000 to 1.

In yet other embodiments, the dispersed liquid crystal microdomains are immobilized within the material containing the dispersed liquid crystal microdomains. In some such embodiments, microdomains may contain a polymer adsorbed to the surface of the microdomains. In certain of these embodiments, the microdomains are immobilized by either covalent bonding of the polymer to a separate solid surface or electrostatic forces between the polymer and the separate solid surface. In other embodiments in which the dispersed liquid crystal microdomains are immobilized, the material containing the dispersed liquid crystal microdomains may be dehydrated, and may include without limitation hydrophilic polymer networks or a gel formed from colloids or polymers. In some such embodiments, the invention further includes an absorbent material placed in contact with the material containing the dispersed liquid crystal microdomains.

In some embodiments, the liquid crystal microdomains are dispersed in water over a surface that contains depressions (wells), and the surfaces of the well are treated to generate a repulsive interaction between the well surface and the microdomains. This geometry confines the liquid crystal microdomains to the wells but prevent the adsorption of the microdomains onto the surface of the wells. This confinement can be useful to facilitate the read out of the configuration of the liquid crystal in the microdomains. In a preferred embodiment, the repulsive interactions are achieved by having like surface charges on the liquid crystal microdomains and the well surfaces. In a second embodiment, the repulsive interaction is created by the adsorption of polymers to the surfaces of the liquid crystal microdomains, the well surfaces or both.

The invention may include a variety of different detectors for detecting the anchoring configuration of the liquid crystal microdomains. In some embodiments, the detector uses light-based detection. In some such embodiments, the detector may be a light-based imaging device, including without limitation a polarized light-based imaging device or a fluorescence-based imaging device. In other such embodiments, the detector may detect scattered light or transmitted light. In some embodiments, the detector includes a bright field light source.

In some embodiments, the detector is located on a flow device. A non-limiting example of a flow device on which the detector may be located is a flow cytometer. The flow cytometer may use a number of possible detection modes, including without limitation light scattering or fluorescence-based mode of detection.

Various liquid crystals may be employed in the dispersed liquid crystal drops of the present invention. Examples of suitable liquid crystals, include, but are not limited to, 4-cyano-4'-pentylbiphenyl (5 CB), 7 CB, and 8 CB, and E7 and TL205. A large listing of suitable liquid crystals is presented in "Handbook of Liquid Crystal Research" by Peter J. Collings and Jay S. Patel, Oxford University Press, 1997, ISBN 0-19-508442-X. Polymeric liquid crystals are also suitable for use in the device and methods of the present invention. Because the devices and methods of the present invention may include contacting the liquid crystal with aqueous test solutions, preferred liquid crystals employed in the invention should be insoluble in water or have very limited solubility in water. Additionally, preferred liquid crystals employed in the invention should not react with water.

In certain embodiments of the present invention, the liquid crystal comprising the droplets is 4-cyano-4'-pentylbipheny-1 (5 CB). Although various types of liquid crystal may be employed, nematic and thermotropic liquid crystals are preferred. However, smectic liquid crystals formed from 8 CB are also suitable for use in the present invention. Suitable liquid crystals further include smectic C, smectic C*, blue phases, cholesteric phases, smectic A, and polymeric liquid crystals.

Changes in liquid crystal ordering within liquid crystal droplets are influenced by the size of the droplets, reflecting a subtle competition between bulk and interfacial physiochemical factors (Gupta et al. Angew. Chem. Int. Ed. 2008, 48, 1652-55). In addition, the size of the droplets may be a factor in droplet coalescence and thus the stability of liquid crystal dispersions (Heppenstall-Butler et al. Liquid Crystals 2005, 32, 77-84). The preferred size for the liquid crystal microdomains of the present invention is a minor axis of between about 0.5 µm and about 200 µm, with a more preferred size being a minor axis of between about 1 µm and about 10 µm. The most preferred size for the liquid crystal droplets of the present invention is a minor axis of between about 2 µm and about 4 µm.

In certain embodiments, the material containing the dispersed liquid crystal droplets is an emulsion of liquid crystal droplets within another liquid, preferably within an aqueous buffer solution. The buffer solution should be LPS free, to prevent interference with the LPS assay of the present invention. The aqueous solution may also be buffer free. Although a variety of standard buffer solutions would be suitable, a preferred LPS free buffer solution for use in the invention is phosphate buffered saline (PBS).

The volume ratio of the LC to the aqueous buffer solution in the LC emulsions of these embodiments can vary. However, it is preferred that the ratio of the initial volume of LC to the volume of aqueous buffer within the emulsion be substantially less than one to one, preferably less than about 1/10, and most preferably less than about 1/100.

In certain embodiments, the dispersed liquid crystal microdomains within the emulsion are immobilized on a substrate surface. Methods of immobilizing liquid crystal microdomains include without limitation the use of polymers (such as certain polymers having a structure that facilitates both (a) adsorption to a liquid crystal surface interface, and (b) the immobilization of the liquid crystal microdomain onto the substrate surface) to promote the immobilization of liquid crystal droplets on substrate surfaces. Such polymers can be spontaneously adsorbed to the droplet interface from the surrounding aqueous solution. An alternative approach which falls within the scope of the invention is to dissolve the polymer within the LC making up the microdomains, and to let it adsorb to the interface from the liquid.

The presence of the polymer at the interfaces of the droplets can be exploited to immobilize liquid crystal droplets on the substrate surface through covalent bond formation or through non-covalent interactions. Examples of non-covalent interactions that could be used to immobilize the liquid microdomains onto the substrate surface include without limitation electrostatic attractions, hydrophobic interactions, dative interactions, coordination bonds, metal-mediated interactions, or other interaction between the multifunctional polymer and the substrate surface.

In some embodiments, the immobilization of the LC microdomains to the substrate is further facilitated by the presence of a chemically functionalized surface on the substrate surface that is capable of interacting with the polymer adsorbed to the droplet interface. Further, the functionalized surfaces may be designed to pattern the immobilization of liquid crystal droplets on the surfaces as needed to further facilitate the present method.

In other embodiments, the material containing the dispersed liquid crystal microdomains is a solid or semi-solid. In some such embodiments, the LC droplets could be fixed within a material through which an aqueous test sample could flow, affecting the anchoring configuration of the fixed droplets as it contacts the droplets. Preferred materials for such embodiments are polymeric hydrogels that do not trigger an anchoring configuration change in LC droplets or a resulting optical response. As one skilled in the art would recognize, there are a number of ways such polymeric hydrogels containing dispersed liquid crystal droplets could be synthesized. One method to make such materials would be to cross-link a hydrogel about a dispersion of LC droplets using photo or chemical methods. Another approach would be to impregnate a hydrogel gel with isotropic mixture of a volatile solvent and LC-forming compound. Upon evaporation of the volatile solvent, the mesogen will phase separate to form LC droplets within the gel. This procedure is well-known in the art and is used to prepare dispersions of LC droplets in polymeric networks used in LC displays.

The gels may also be formed physically, such as through hydrogen bonding and hydrophobic interactions. Gels formed by amphiphile polymers such as pluronic polymers are suitable for these embodiments of the inventions. In other embodiments, the LC microdomains may be formed within a composite material, where one interface of the microdomains is exposed to the aqueous sample containing LPS. In a preferred embodiment the composite material is a colloid-in-liquid crystals gel comprised of micrometer-sized LC domains. In other preferred embodiments, the LC microdomains are supported on the surface of a solid material across which the LC domains do no spontaneously spread. An example of such a material is a silanized glass microscope slide that supports LC microdomains. In other embodiments the LC microdomains are defined by topographical features on surfaces, such as step edges and walls of microwells. In other preferred embodiments, electric fields and optical fields are used to trap or move the LC microdomains to enable detection of the analyte.

In certain embodiments using polymeric hydrogels, the hydrogel can be dehydrated using any of a number of dehydration methods known in the art. In these embodiments, rehydration of the hydrogel can be used to draw the aqueous test sample containing LPS into contact with the dispersed LC droplets. In other embodiments using polymeric hydrogels, the hydrogel can be hydrated prior to introduction of the sample, and an absorbent material can be placed downstream of the hydrogel in order to draw the sample across the dispersed LC droplets using capillary forces. In other embodiments of the invention, the sample can be placed onto the top surface of a material containing the LC microdomains, or the sample can be flowed through a microfluidic channel to contact the LC microdomains, or the sample can be placed into a well to contact the LC microdomains. In other embodiments of the invention, a device is contacted with an aqueous solution to remove LPS from the surface of the device, and LPS is detected within the aqueous solution by contact with micrometer-sized LC domains.

The liquid crystal-based sensor of the present invention also includes a detector capable of detecting and reporting either the anchoring configuration of the liquid crystal microdomains or the number of defects in the liquid crystal microdomains, as described above. Because anchoring configuration of liquid crystal droplets can be determined using either polarized microscopy or bright field microscopy, an optical microscope can be used as the detector in certain embodiments.

More generally, the scope of the invention includes the use of polarized light or non-polarized light to detect the configuration of the LC within the droplet. Organized arrays of LC microdomains can also define optical band-gap materials and the scope of the invention includes use of such collective optical behaviors exhibited by arrays of LC microdomains. Because defects formed within the LC droplets scatter light, it is also possible to detect the configuration of LC within the LC microdomains by measurement of the scattering of non-polarized light. The light can be monochromatic, white light, or colored light comprising a mixture of wavelengths, and all can be employed in the practice of this invention.

The scope of the invention includes the use of the LC microdomains as wave-guides. For example, by including one or more fluorescence molecules within the LC microdomain, it is possible to determine the configuration of the LC within the microdomain because the LC configuration will guide light to and from the fluorescence molecules. For example, the radial configuration of the LC droplet will guide light to the center of the droplet, and give rise to a bright fluorescence spot at the center of the droplet. The bright fluorescence spot can be used to detect that the droplet has assumed a radial configuration. Thus methods that detect fluorescence intensity and image fluorescence emissions fall within the scope of the current invention.

Figure 3:
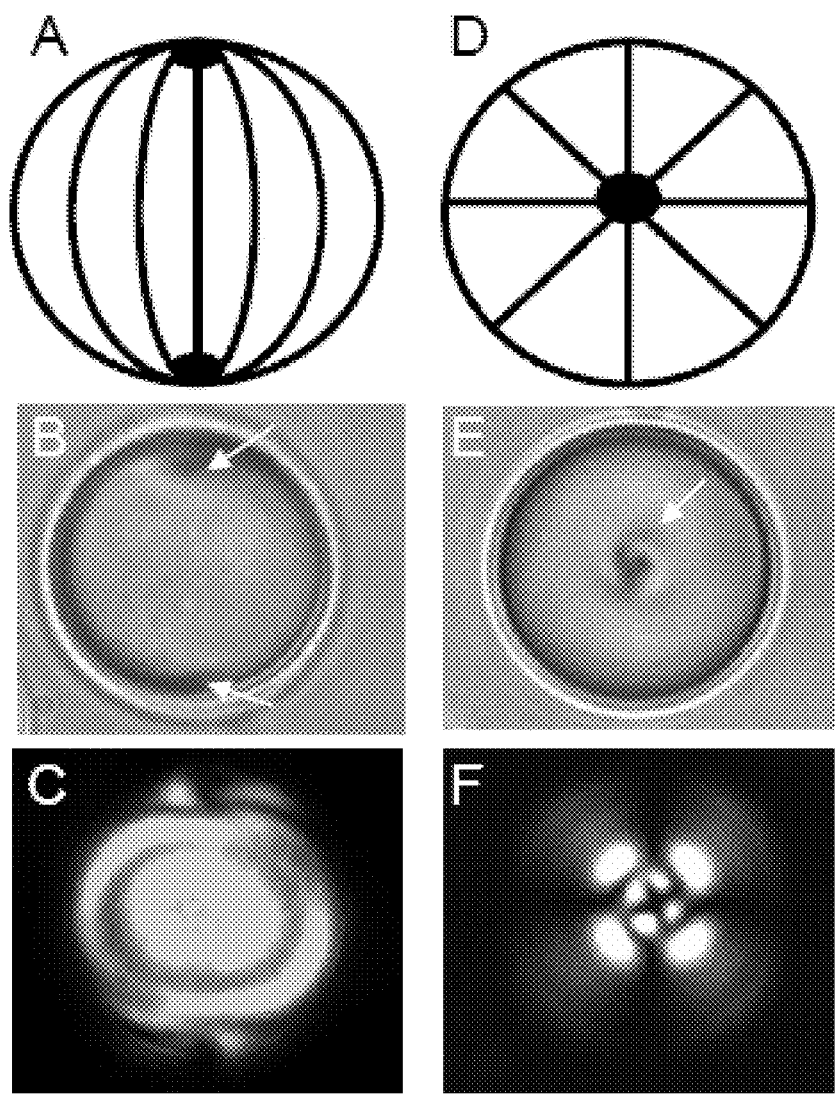
FIG. 3A is a schematic illustration of the bipolar anchoring configuration of liquid crystal droplets.
FIG. 3D is a schematic illustration of the radial anchoring configuration of liquid crystal droplets. The remaining parts of FIG. 3 are bright-field (3B, 3E) and polarized (3C, 3F) optical micrographs of polymer-encapsulated 5CB droplets with diameters of 8.0±0.2 μm having bipolar (3B, 3C) and radial (3E, 3F) anchoring configurations. Point defects in the LC droplets are indicated by white arrows.

In a bipolar anchoring configuration, the director (local alignment of LC) follows the contour of the surface of the droplet, connecting the two diametrically opposed point defects (called boojums) at the poles of the LC droplets (FIG. 3A). The presence of two point defects in the bright-field image (FIG. 3B) and the corresponding characteristic polarized image showing a relatively uniformly bright disk (FIG. 3C) confirms the bipolar anchoring configuration in LC droplets.

In contrast, in a radial anchoring configuration, the director radiates from the center of the droplet and is normal to the interface. The LC droplet has one point defect located at the center of the droplet (FIG. 3D), which can be seen in a bright field image (FIG. 3E). When viewed under a polarized light microscope, the optical appearance of the radial anchoring configuration droplet is invariant when viewed at differing angles, and shows a characteristic isogyre (dark cross-shaped pattern) (FIG. 3F), while the bipolar configuration does not (FIG. 3C).

Accordingly, the detector used in certain aspects of the present invention may be an optical microscope that is fitted with specialized parts to enable the viewing of polarized or bright field images. Such parts may include, but are not limited to, bright field light sources appropriate for bright field microscopy and cross-polarizers for use in polarized microscopy. Other parts that may be used in such detectors would be readily recognized by those skilled in the art.

Figure 14:
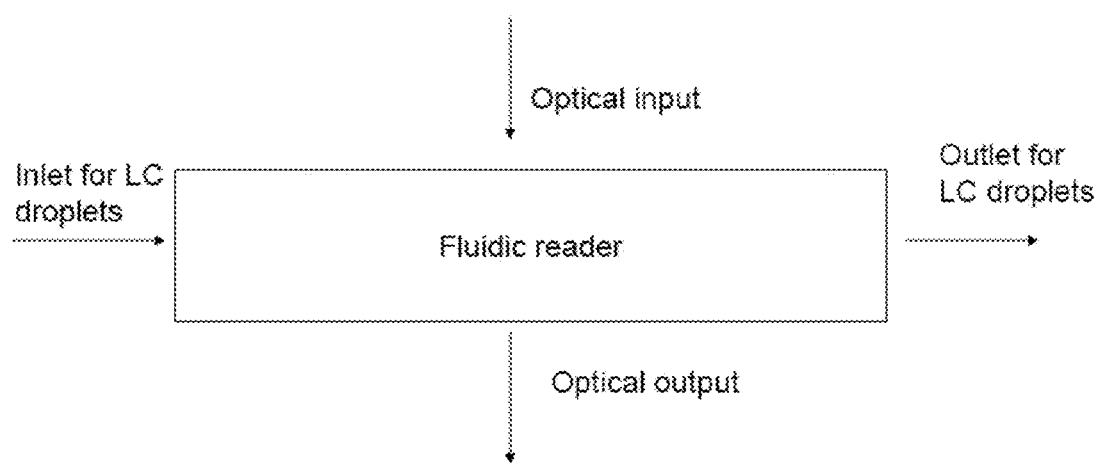
FIG. 14 is a schematic illustration of a flow device through which the aqueous dispersion of LC droplets is flowed, and optical methods (such as scattering of light, imaging, fluorescence detection) are used to determine the configuration of the LC within the droplets.
Figure 15:
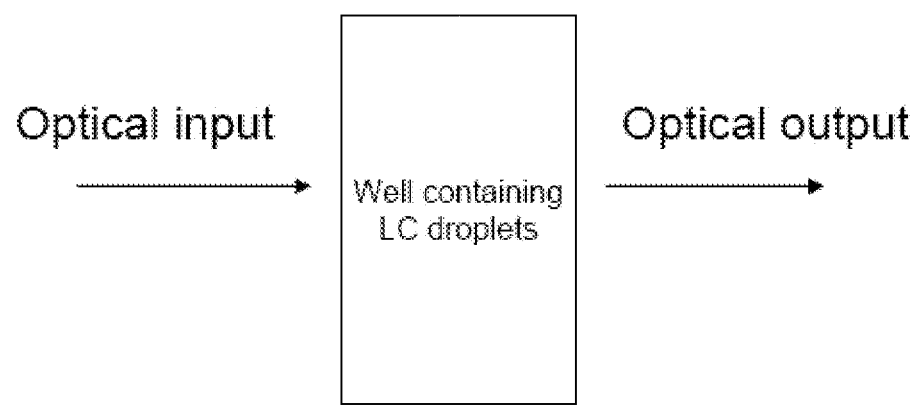
FIG. 15 is a schematic illustration of an embodiment of the invention in which the LC droplets are placed into the well for analysis using light.

More generally, devices that optically probe the LC microdomains, and record a signature that changes with the internal configuration of LC within the LC microdomains can be used for the practice of this invention. These devices can comprise a flow channel, where the LC microdomains are introduced to the device through an inlet and removed through an outlet (a fluidic reader, FIG. 14), or the devices can comprise a geometry that possesses a single inlet, such as a cuvette used in a spectrophotometer. The invention includes use of a spectrophotometer to determine the configuration of the LC droplets through changes in the intensity of light that is transmitted through the LC domains. Such devices may also comprise one or more wells or microwells to contain the LC microdomains for optical probing (FIG. 15).

In certain other embodiments, a fluidic reader such as a flow cytometer may be used as the detector in the liquid-crystal based sensor. In a flow cytometer, a beam of light is directed onto a hydro-dynamically focused stream of fluid, which could include the liquid crystal emulsion contained in certain embodiments of the invention. Multiple detectors are aimed at the point where the stream passes through the light beam, both in line with the light beam (measuring forward scatter or FSC) and perpendicular to the light beam (measuring side scatter or SSC). The liquid crystal droplets passing through the beam scatter the light both forward and to the side, and this scattering of light can be detected by analyzing the fluctuations in brightness at each detector.

The inventors have determined that the ratio of side-scattering to forward scattering of light in liquid crystal droplets undergoing flow cytometry analysis depends on the anchoring configuration of the droplets. In addition, the higher degree of symmetry present in the LC droplets having the radial anchoring configuration results in a tighter distribution of light scattering data for such droplets as compared to liquid crystal droplets having the bipolar anchoring configuration. This result is consistent with our present model of anchoring configuration, because light scattering from a radial droplet should be invariant to the rotation of the droplet, whereas the scattering from bipolar droplets depends on the orientations of the droplets and the incident light. The use of flow cytometry as a detector in the sensor of the present invention potentially provides a rapid and high throughput method to detect and quantify the relative populations of radial and bipolar LC droplets, and thus to detect and quantify the LPS in an aqueous test sample. More generally, the scope of the invention includes measurement of the scattering of light from the LC domains to determine the configuration of the LC within the LC microdomains. A wide range of commercial devices permit measurement of scattering of light from objects, including light scattering instruments.

As the skilled artisan would recognize, there are additional types of detectors in the present invention for detecting and reporting the anchoring configuration of the liquid crystal droplets. For example, as mentioned above, because of differences in fluorescence properties between liquid crystal droplets having the two anchoring configurations, a fluorescence-detecting flow cytometer or a fluorescence microscope may be used as a detector. In another example, because liquid crystals having different anchoring configurations have different dielectric properties, the detector may include an electrophoresis or dielectrophoresis apparatus or other device for applying an electric field. The anchoring configurations could then be detected by observing differences in movement of the liquid crystal droplets within the electrical field over time.

In some embodiments, the sensor of the present invention includes an aqueous test sample placed in contact with the liquid crystal microdomains. The aqueous test sample is the solution that is to be tested for the presence and quantification of LPS. As shown in the examples below, the inventors have found that varying the volume ratio of the LPS test sample to the liquid crystal in the microdomains (and thus the volume ratio of the test solution to the LC contained within an emulsion) substantially affects the sensitivity of the sensor. In particular, starving the LPS at the aqueous-LC interface by decreasing the number of LC emulsion droplets per unit volume of LPS test sample used in the system increases the sensitivity of the method.

In preferred embodiments, the volume ratio of the aqueous test sample to the liquid crystal in the microdomains that contact the test sample is greater than or equal to about 100 to 1. Greatly increased sensitivity is achieved in the invention by increasing the ratio of the sample volume to volume of liquid crystal in the micrometer-sized domains. At a more preferred volume ratio of the aqueous test sample to liquid crystal in the microdomains greater than or equal to about 1,000 to 1. The highest sensitivity is achieved when the volume ratio of the aqueous test sample to the liquid crystal within the micrometer-sized domains is greater than or equal to about 40,000 to 1. The upper limit on this ratio is defined by the need to have at least one microdomain of liquid crystal in order to practice the invention.

In some embodiments of the invention, the LC is added directly to the sample and a dispersion of LC emulsion droplets is generated within the sample volume. In a preferred embodiment, the emulsion of LC droplets is created by sonication or passage of the sample containing LC through an emulsifier. Many machines are described in the existing literature for formation of emulsions, and use of these machines is contemplated within the context of this invention.

In a second aspect, the invention is a method for detecting and/or quantifying an analyte, preferably endotoxin lipopolysaccharide (LPS) or lipid A, in a test sample. The method includes providing one or more liquid crystal microdomains, preferably dispersed and having a minor axis of between about 0.5 µm and about 200 µm, contacting the microdomains with a test sample, preferably an aqueous test sample, and using a detector to detect the anchoring configuration of or to determine the number of defects in the liquid crystal microdomains. More preferably, the liquid crystal microdomains have a minor axis of between about 1 µm and about 10 µm, and most preferably, the liquid crystal microdomains have a minor axis of between about 2 µm and about 4 µm.

In some embodiments, the liquid crystal microdomains are provided in a liquid crystal in water emulsion, and the liquid crystal microdomains are liquid crystal droplets. A preferred volume ratio of the aqueous test sample to the liquid crystal contained within the liquid crystal emulsion is greater than or equal to about 100 to 1, a more preferred volume ratio of the aqueous test sample to the liquid crystal contained within the liquid crystal emulsion is greater than or equal to about 1,000 to 1, and a still more preferred volume ratio of the aqueous sample to the liquid crystal contained within the liquid crystal emulsion is greater than or equal to about 40,000 to 1. In certain such embodiments, the emulsion is LPS free, and the step of providing the liquid crystal in water may include providing an LPS free buffer.

A variety of methods may be used to detect the anchoring configuration of the liquid crystal microdomains, including without limitation optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, and using a cuvette in a detector. Further details are described in detail above in connection with the description of the liquid crystal-based sensor.

In further embodiments, the method includes an additional step of using a microfluidic device to deliver the sample to the detector. In yet other embodiments, all pipettes, plasticware, vessels, and other devices used in performing the method are LPS free.

In certain embodiments, the method includes the additional step of quantifying the analyte, preferably LPS or lipid A, present in the aqueous test sample. This can be done in a number of ways. For example, the inventors have demonstrated that the percentage of radial or bipolar anchoring configuration droplets after contact with the aqueous test solution depends on the quantity of LPS in the test solution. Accordingly, quantification could be done by correlating anchoring configuration percentages to the percentages obtained from standardized samples of known concentration. As one skilled in the art would appreciate, quantification of LPS is not limited to such direct correlation, and there would be many ways to quantify LPS in a test sample from detector data. As a non-limiting example, a computer program based on testing of LPS solutions of known concentration could be developed to analyze light scattering or fluorescence data from flow cytometry to directly calculate the quantity of LPS present in a test sample without calculating the percentages of droplets having a given anchoring configuration.

In a third aspect, the invention is directed to a method of making a liquid crystal-based sensor for detecting and/or quantifying an analyte, preferably endotoxin lipopolysaccharide (LPS) or lipid A, in a test sample. The method includes (a) providing a material comprising one or more dispersed liquid crystal microdomains, preferably having a minor axis of between about 0.5 µm and about 200 µm, and (b) providing a detector capable of detecting and reporting the anchoring configuration of or the number defects in the liquid crystal within the microdomains. In this aspect, the liquid crystal microdomains, the materials containing the dispersed microdomains, and preferred detectors are described in detail above in connection with the description of the liquid crystal-based sensors.

In further embodiments of this aspect of the invention, the material comprising the dispersed liquid crystal droplets is a liquid crystal emulsion. As one skilled in the art would recognize, the emulsion can be made in a number of ways. Preferably, the emulsion is made by sonicating and vortexing a mixture containing liquid crystal and LPS free buffer, and more preferably, the sonication and vortexing process are alternated a number of times, most preferably through twelve or more cycles of sonicating and vortexing. In other embodiments, the emulsions are made using microfluidic channels with flow focusing, or made by passing the liquid crystals and aqueous solution through an orifice or orifices.

In other embodiments, the material comprising the dispersed liquid crystal microdomains is a composite material comprising the microdomains. The composite material could be a gel, such as a gel prepared by dispersing colloids within the liquid crystal, leading to so-called colloid-in-liquid crystal gels. In other embodiments, the microdomains could be formed within a polymeric or inorganic material. In other preferred embodiments, the polymeric material has hydrophilic segments that give rise to formation of hydrogels containing the micrometer-sized liquid crystal microdomains. The invention covers making of the material, which includes forming a hydrogel about dispersed liquid crystal droplets. Further details of this process are discussed above.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Materials and Methods

As applicable and unless otherwise noted, the following materials and methods were used throughout the following examples.

Materials. Endotoxin (lipopolysaccharide (LPS) from *E. Coli* O127:B8 and *E. Coli* O111:B4), lipid A (diphosphoryl from *E. Coli* F583), and sodium dodecylsulfate (SDS) were purchased from Sigma-Aldrich (St. Louis, Mo.). DLPC and DOPC were purchased from Avanti Polar Lipids, Inc. (Alabaster, Ala.). Octadecyltrichlorosilane (OTS), methanol, methylene chloride, sulfuric acid, hydrogen peroxide (30% w/v), and heptane were obtained from Fisher Scientific (Pittsburgh, Pa.). Ethanol was obtained from Pharmco-Aaper (Brookfield, Conn.). The LC, 4'-pentyl-4-cyanobiphenyl (5CB) was obtained from EM Sciences (New York, N.Y.). LAL reagent water was purchased from Associates of Cape Cod, Inc. (E Falmouth, Mass.). Endo Trap red Equilibration Buffer (PBS buffer) was purchased from Profos AG (Regensburg, Germany). Neptune pipette tips (no detectable endotoxin) were purchased from Continental Lab Product, Inc. Polystyrene tubes (certificated nonpyrogenic tubes) were purchased from Becton Dickinson Labware (Franklin lakes, NJ). Glass microscope slides were Fisher's finest premium grade obtained from fisher scientific. Gold specimen grids (20 $\mu$m thickness, 50 $\mu$m wide bars, and 283 $\mu$m grid spacing) were obtained from Electron Microscopy Sciences (Fort Washington, Pa.).

Preparation of LC-Filled Grids for Example 2. Glass microscope slides were cleaned according to published procedures and coated with OTS. The quality of the OTS layer was assessed by checking the alignment of 5CB confined between two OTS-coated glass slides. Any surface not causing homeotropic anchoring (perpendicular alignment of 5CB) of 5CB was discarded. Gold specimen grids that were cleaned sequentially in methylene chloride, ethanol, and methanol were placed onto the surface of OTS-coated glass slides. Approximately 1 $\mu$L at of 5CB was dispensed onto each grid and then excess LC was removed by contacting a capillary tube with the droplet of 5CB. Each LC-filled grid was equilibrated at ambient temperature and subsequently immersed in the aqueous solution of interest at 25° C.

Preparation of Standardized Aqueous Dispersion of LPS (Aqueous Test Solutions). LPS powder was dissolved in either LAL reagent water (for LAL comparison tests) or PBS buffer (for testing of the present invention) at room temperature. For newly reconstituted LPS solution (such as 1 mg/mL or 100 $\mu$g/mL LPS concentration; 1 to 5 mL total volume), the first solution was vortex mixed at 2500 rpm for 4 minutes first and after each serial dilution for 45-second vortex mixing at same speed to reach final desired concentration. For LAL comparison tests, a kinetic turbidimetric LAL assay (Kinetic Turbidmetric (KTA2) LAL assay, Charles River Laboratories International, Inc.) with an effective LPS detection range sensitivity of 100-0.001 EU/mL (approximate 10000-0.1 pg/mL) was performed in the Waisman Clinical Biomanufacturing Facility Laboratory, University of Wisconsin.

Preparation of Aqueous Dispersion of DLPC, DOPC, and SDS for Example 5. Vesicular dispersions of DLPC and DOPC were prepared according to published procedures. Briefly, DLPC or DOPC were dissolved in chloroform and dispensed into glass vials. The phospholipid-containing chloroform solution was evaporated under a stream of $N_2$, and the vial containing the lipids was then placed under vacuum for at least 2 hours. The dried lipid was resuspended in PBS buffer solution. Subsequent sonication of the lipid suspension using a probe untrasonicator resulted in a clear solution. The phospholipid solution was then extruded through a 0.22 $\mu$m pore filter (Millipore) before use. For all DLPC, DOPC, and SDS solutions, PBS buffer was used as the solvent.

Preparation of LC Emulsions. The LC emulsions in PBS were formed by sonicating and vortexing a mixture of 2 $\mu$L 5CB with 1 mL PBS buffer at 25° C. Twelve cycles of alternating 10-second vortex mixing (at 2500 rpm) and 10-second sonication resulted in milky white LC-in-PBS emulsions. The LC droplets of the emulsions were spherical, with a radius size range of 2-4 $\mu$m and were visually observed to be stable against coalescence at least for 3 hours. We prepared the LC emulsions within 3 hours of their use, to avoid potential changes in the distribution of drop sizes associated with coalescence and ripening of the emulsions (FIG. 1C).

Determination of the Orientation of Liquid Crystals by Polarized Light microscopy. The orientation of LC filled within Au grids in Example 2 was observed by using an Olympus BX60 microscope with crossed polarizers (transmission mode). Orthoscopic examinations were performed with the source light intensity set to 50% of full illumination and the aperture set to 10% to collimate the incident light. Homeotropic (perpendicular) alignment of a LC was determined by insertion of a condenser below the stage and a Bertrand lens above the stage allowed conoscopic examination of the specimen. An interface pattern consisting of two crossed isogyres confirmed the homeotropic alignment. Images were captured with a microscope-mounted digital camera (Olympus C-4000 Zoom) set to an f-stop of 2.8 and a shutter speed of 1/320 s. The configuration of the LC within the LC emulsions was observed under an Olympus IX71 inverted microscope under an objective power of 100× (an oil lens). Brightfield and polarized images of the LC emulsions were collected with a Hamamatsu 1394 ORCA-ER CCD camera (Bridgewater, N.J.) connected to a computer and controlled through SimplePCI imaging software (Compix, Inc., Cranberry Twp., N.J.).

Size Distribution of the LC Emulsions. Size distribution of the LC emulsions upon contact with various analyte solutions of interest were measured and calculated from the optical micrographs taken under the brightfield microscopy by using ImageJ software. A 120×96 μm² viewfield area under an objective power of 100× usually attains 5 to 10 LC emulsion droplets under the focal plane of interest.

Example 2

Figure 4:
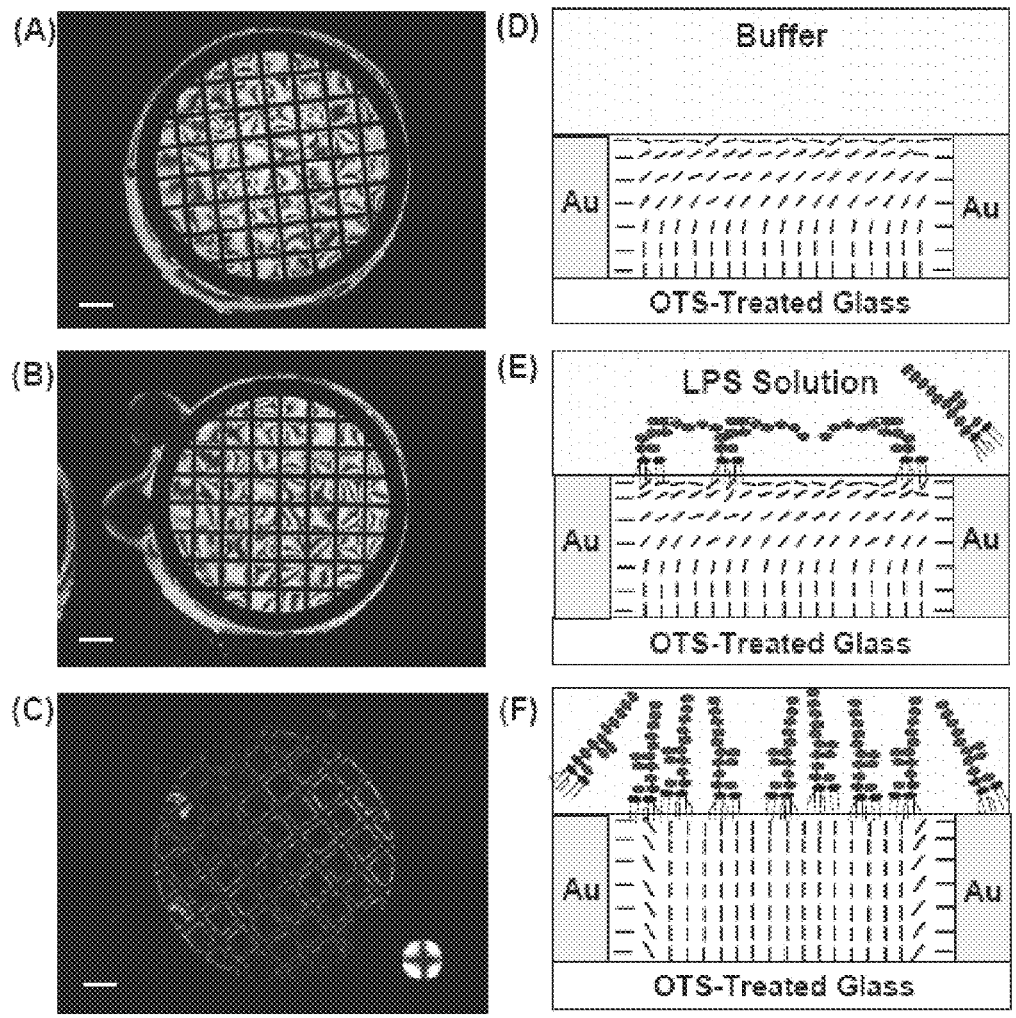
FIG. 4 shows optical micrographs (A-C) and schematic side view illustrations (D-F) of 5CB confined to specimen Au grids.

Spontaneous LPS Adsorption onto Aqueous-LC Interfaces in Grid-Based LC Device In this example, the inventors used a grid-based (non droplet-based) LC device to demonstrate that spontaneous adsorption of LPS at the aqueous-LC interface can trigger an ordering transition in the LC from a parallel orientation (planar anchoring) to a homeotropic (perpendicular) anchoring. These experiments were performed by hosting the LC within metallic grids placed on an OTS-treated glass microscope slide. The result of these experiments are shown in FIG. 4.

Upon contact with PBS buffer, the LC at the interface with the buffer maintained a planar anchoring with parallel orientation (FIG. 4D). This is confirmed by the optical micrograph (FIG. 4A). Upon contact with 2 mL 1 milligram/mL LPS in PBS buffer for less than two minutes, the LC at the interface with the buffer switched to homeotropic anchoring with perpendicular orientation (FIG. 4F). This is confirmed by the optical micrograph (FIG. 4C). Note the characteristic isogyre obtained by conoscopic imaging in the lower right inset in FIG. 4F. After 24 hours of contact with 2 mL of 1 micrograms/mL LPS in PBS buffer, the LC still exhibited the original planar anchoring with parallel orientation, as confirmed by optical micrographs (FIGS. 4E and 4B).

The results show that LPS spontaneously adsorbs at the aqueous-LC interface and dictates the LC anchoring transition from planar to homeotropic alignment at an LPS concentration of 1 mg/mL within a 1 min time interval. However, this experimental setup is insensitive to LPS concentrations of less than 1 mg/mL in an aqueous solution. In particular, even after 24 hrs, it is not possible to detect 1 microgram/ml of LPS in the sample using this grid geometry. As the following examples show, substantially greater sensitivity can be achieved by using the LC droplet-based sensors and methods of the present invention.

Example 3

Spontaneous LPS Adsorption onto Aqueous-LC Emulsion Interfaces

Figure 5:
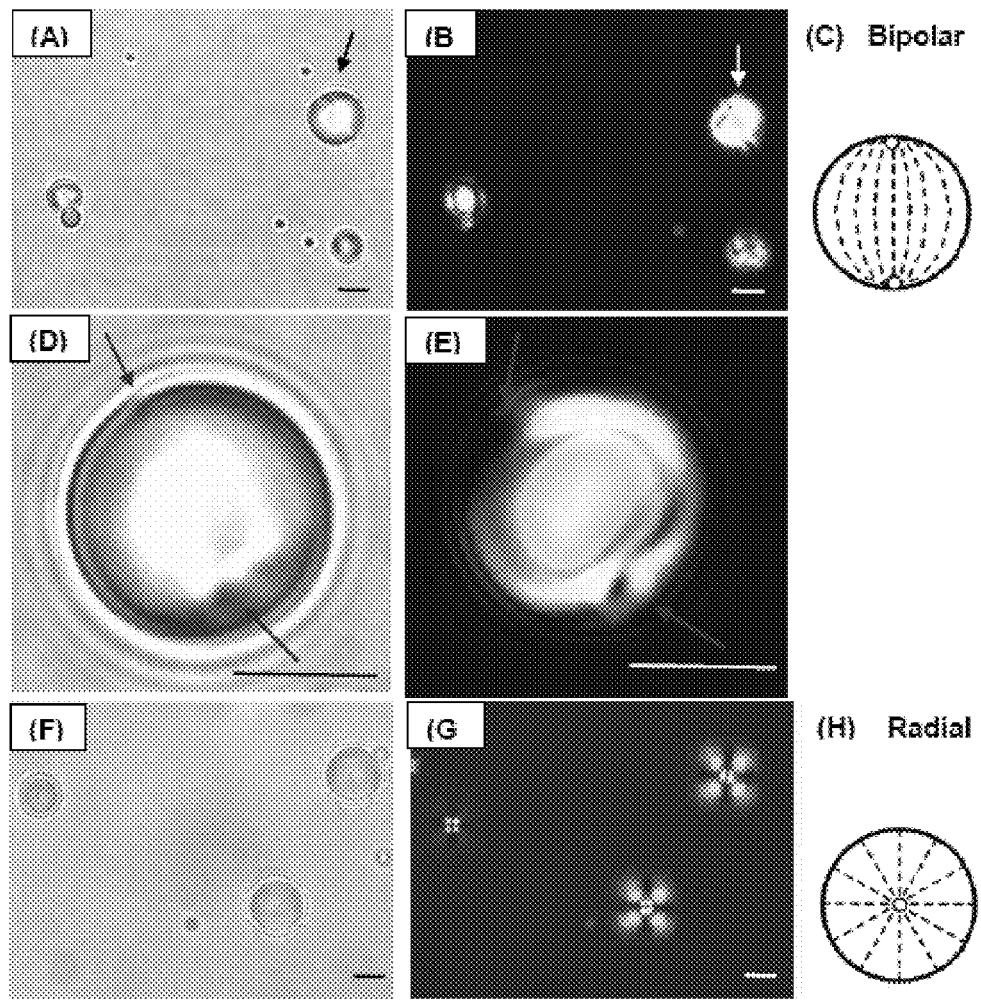
FIG. 5 shows anchoring configuration profiles (C, H) and optical micrographs (A, D, and F are bright-field micrographs, B, E, and G are polarized micrographs) of 5CB-PBS emulsions (10 μL 5CB emulsions with 40 μL PBS buffer) (A-E) and 5CB-LPS (1 mg/mL LPS in PBS buffer) emulsions (10 μL 5CB emulsions with 40 μL LPS solution) (F-H). The PBS buffer contained less than 2 pg/mL LPS as certificated by the supplier. Planar anchoring of 5CB at the interface of a 5CB-PBS emulsion droplets results in a bipolar configuration with two surface defects (boojums). Arrows have been added to FIGS. A, B, D, and E to highlight the bipolar configuration by locating the boojums at the droplet interface. In the 5CB-PBS emulsions, a transition to a single point defect (hedgehog) at the droplet center occurs upon contact with 1 mg/mL LPS, leading to radial anchoring of 5CB at the interface (F). The characteristic isogyre in the polarized micrograph shown at FIG. 5G is a signature of radial anchoring configuration in the droplet. Scale bars correspond to 5 μm.

In this example, the inventors conducted initial experiments to demonstrate that the LC droplet-based sensors and methods of the present invention could be used to detect LPS in an aqueous sample. 10 μL of LC emulsion were mixed with either 40 μL 1 mg/mL LPS or 40 μL LPS free PBS buffer (control). As expected, in the absence of LPS (control), the LC droplets maintained a bipolar anchoring configuration (FIG. 5C), as evidenced by the two surface defects seen under bright field microscopy (FIG. 5A, 5D) and polarized microscopy (FIG. 5B, 5E). Note also the lack of an isogyre in the polarized images (5B, 5E).

In contrast, when LC emulsion droplets were contacted with 1 mg/mL LPS in PBS buffer, they rapidly (in less than one minute after contact) converted to the radial anchoring configuration (FIG. 5H), as evidenced in bright field micrographs showing a single point defect (FIG. 5F) in each droplet and characteristic isogyres seen in polarized micrographs (FIG. 5G). These results demonstrate that LPS spontaneously adsorbs at aqueous-LC emulsion interfaces to cause an ordering transition which is easily observed using optical methods.

Example 4

Increased Sensitivity to and Quantification of LPS by LC Emulsion Droplets

This example shows how decreasing the volume ratio of the LC emulsion (and thus volume of LC within the droplets of the emulsion) to the aqueous test solution substantially increases the sensitivity of the method. In addition, the example demonstrates the feasibility of using anchoring configuration data to quantify the LPS present in an aqueous test solution.

Figure 6:
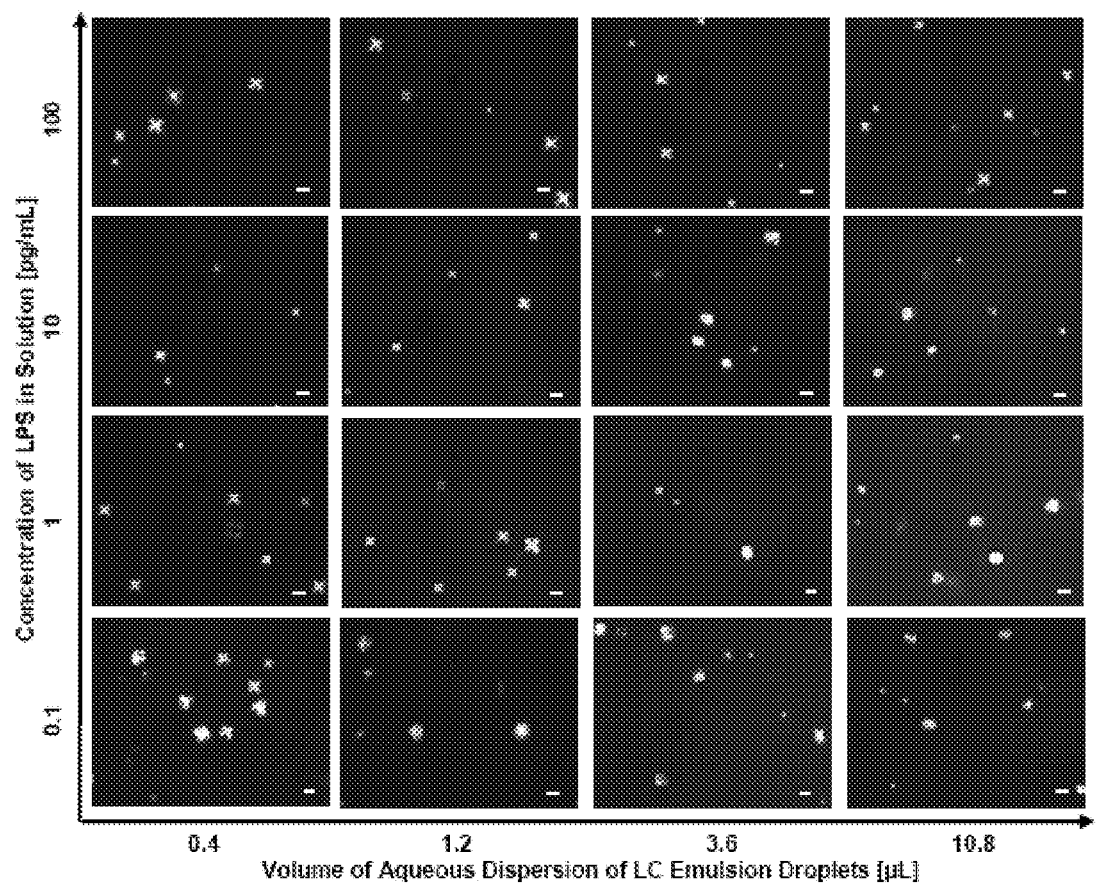
FIG. 6 shows polarized microscopy images of LC droplets from analysis systems containing varying volumes of LC emulsions (Y axis) and varying concentrations of LPS in the test solution (X axis). The volume of the LPS test solution used in the systems is fixed at 40 μL. Starvation of LPS at the aqueous/5CB emulsion interface by decreasing the number of LC emulsion droplets per unit volume of the solution of LPS used in the system results in increased fraction of the LC emulsion droplets with the radial configuration as seen in the polarized microscopy images. Scale bars correspond to 5 μm.

Four LPS test solutions, having concentrations of 0.1 pg/mL, 1 pg/mL, 10 pg/mL, and 100 pg/mL LPS, were used in this example (FIG. 6, left axis). First, the inventors contacted 10.8 μL of LC emulsion with a 40 uL volume of each of the four different LPS test solutions, and observed the droplets in the four resulting test systems using polarized microscopy (FIG. 6, right column). Note that the transition from radial to bipolar anchoring (as shown by isogyre appearance) occurred between the 10 pg/mL and 100 pg/mL LPS concentration (FIG. 4, right column). Thus, the sensitivity (LOD) at a 4/1 test sample to emulsion ratio is between 10 and 100 pg/mL LPS. This corresponds to a ratio of sample volume to LC within the microdroplets of at least 1000 to 1.

To demonstrate the increased sensitivity of the method when using larger volume ratios of LPS test sample to LC emulsion, additional tests were done using the same volume (40 uL) of the four standardized LPS test solutions with three smaller volumes of LC emulsion (0.4 uL, 1.2 uL, and 3.6 uL) (FIG. 6, left three columns). Note that as LC emulsion volume decreases, the method becomes more sensitive. This "starvation" effect becomes particularly clear in the test using 1.2 uL of LC emulsion, where all of the droplets show an isogyre in polarized micrographs (indicating radial anchoring configuration) at an LPS concentration of 1 pg/mL (FIG. 6, second column from left, second micrograph from the bottom). Additional reduction in emulsion volume further increases the sensitivity of the method, with the test using 0.4 uL LC emulsion showing sensitivity (a change in anchoring configuration evidenced by isogyre appearance in the micrographs) down to the smallest tested LPS concentration, 0.1 pg/mL (FIG. 6, lower left micrograph). When 0.4 uL of emulsion was used, the ratio of the sample volume to LC in the microdroplets was at least 40,000/1 (See Example 10 for quantification of LC volume in the microdroplets).

The results in FIG. 6 show that decreasing the number of LC emulsion droplets per unit volume of the solution of LPS causes an increasing number of LC emulsion droplets adopt radial anchoring configurations. In addition, the relative number of the droplets showing a radial configuration at a given volume of LC emulsion appears to be related to the concentration of LPS in the test solution. This provides a basis for using the present method to quantify the LPS present in a test solution by comparing anchoring configuration data (i.e. percentage radial configuration) in an unknown test sample to such data from standard LPS samples of known concentration.

Figure 7:
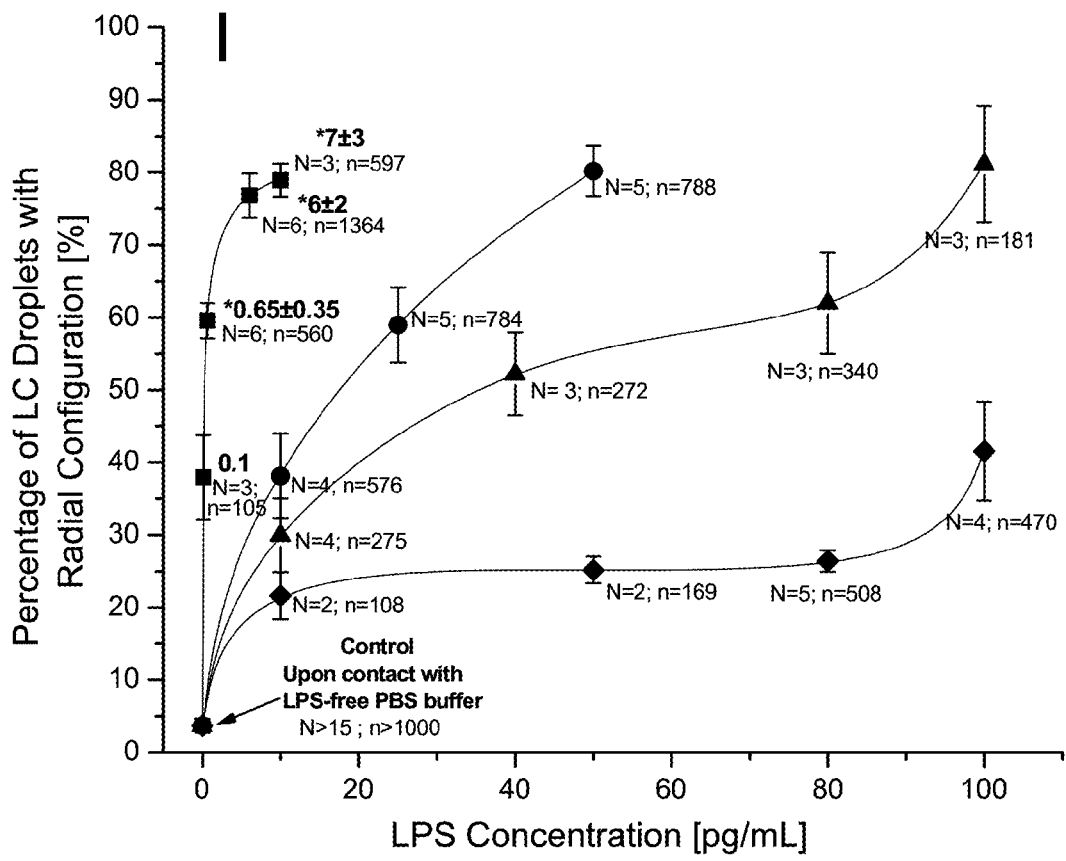
FIG. 7 is a second dose-response curve for LC droplets exposed to LPS in solution. The percentage of radial anchoring configuration droplets (Y axis) is plotted as a function of LPS concentration. The volume of the endotoxin solution was 40 μL and the number of LC droplets in the endotoxin solution was either 8,600 (■), 43,000 (●), 86,000 (▲) or 260,000 (♦). The droplet numbers were determined using flow cytometry. LPS concentrations indicated with stars were all benchmarked against an LAL assay. N indicates the number of independent experiments performed, and n indicates the total number of LC emulsion droplets that were analyzed. The lines are drawn to guide the eye.

To further demonstrate the feasibility of using anchoring configuration data to detect and quantify LPS, the inventors compared the anchoring configuration data (anchoring configuration as a function of concentration of endotoxin) for fifteen different LC emulsion-LPS samples wherein the volume of the endotoxin solution was 40 µL and the number of LC droplets in the endotoxin solution was either 8,600 (square data points), 43,000 (circular data points), 86,000 (triangular data points) or 260,000 (diamond data points). The results are shown in FIG. 7. The droplet numbers were determined using flow cytometry, and endotoxin concentrations indicated with stars were all benchmarked against an LAL assay As the data in both FIG. 7 show, the percentages of radial anchoring configuration increases with the concentration of LPS, and the data also show that the dynamic range of the assay can be varied by changing the ratio of the LC in the system to the sample volume.

In sum, this example demonstrates a sensitivity down to a 0.1-1 pg/mL LPS LOD using the LC-emulsion-based LPS detection methods of the present invention, and also demonstrates that anchoring configuration data obtained using the method could be used to quantify LPS in a test sample.

Example 5

Specificity of LPS-Induced LC Emulsion Anchoring Transition to LPS

This example shows that the high sensitivity of the method for the detection of LPS is specific to LPS. Specifically, the inventors determined that common double-tailed lipids such as DLPC and DOPC and single-tailed synthetic surfactants do not induce reordering of LC droplets at concentrations less than 10 µg/ml, a concentration that is at least six orders of magnitude greater than that leading to a response to LPS endotoxin. The inventors also performed experiments using the lipid portion of endotoxin (lipid A, diphosphoryl from E. Coli F583), and determined that it triggered ordering transitions in the LC droplets in a manner that was indistinguishable from LPS endotoxin.

Figure 8:
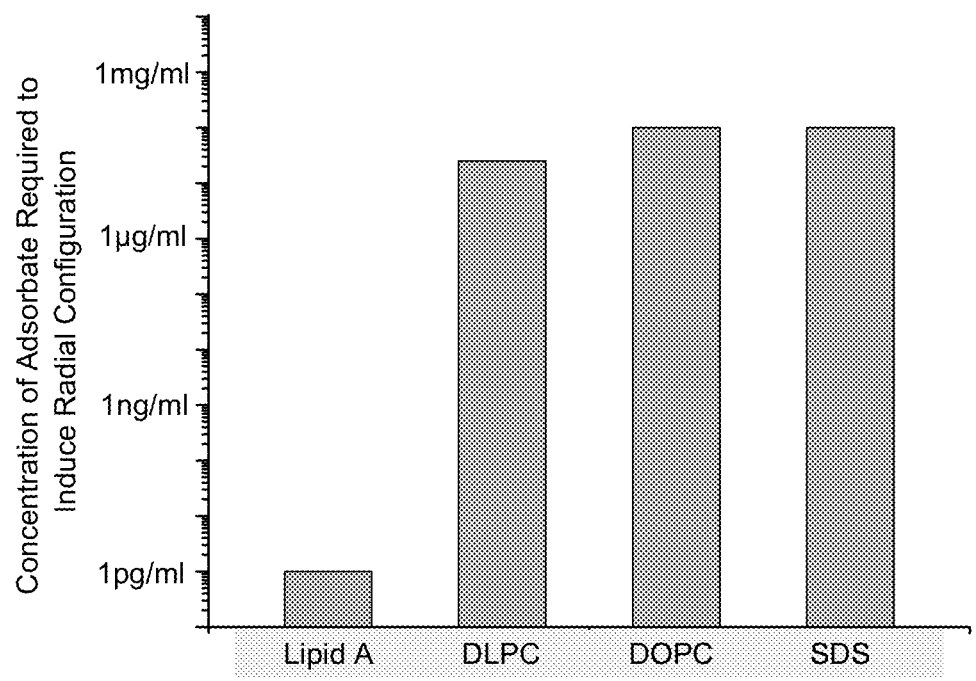
FIG. 8 is a bar graph comparing the concentrations of various lipids or surfactants required to cause LC droplets to adopt a radial configuration. The measurements were performed by adding 8,600 LC droplets to 40 μL of the solution of interest and subsequently analyzing the 5CB droplets under crossed polars. The concentrations indicated are those required to cause at least 60% of the LC droplet to assume a radial configuration. In the absence of the lipids and surfactants, the LC droplets exhibited bipolar configurations.

The inventors compared the concentrations of the lipids DLPC and DOPC and the surfactant SDS required to cause LC droplets to adopt a radial configuration with the concentration of LPS required to cause LC droplets to adopt a radial configuration. The results of the comparison are shown in FIG. 8. The measurements were performed by adding 8,600 LC droplets to 40 µL of the given solution of interest and subsequently analyzing the 5CB droplets under crossed polars. The concentrations indicated are those required to cause at least 60% of the LC droplet to assume a radial configuration. In the absence of the lipids or surfactants, the LC droplets exhibited bipolar configurations.

Figure 9:
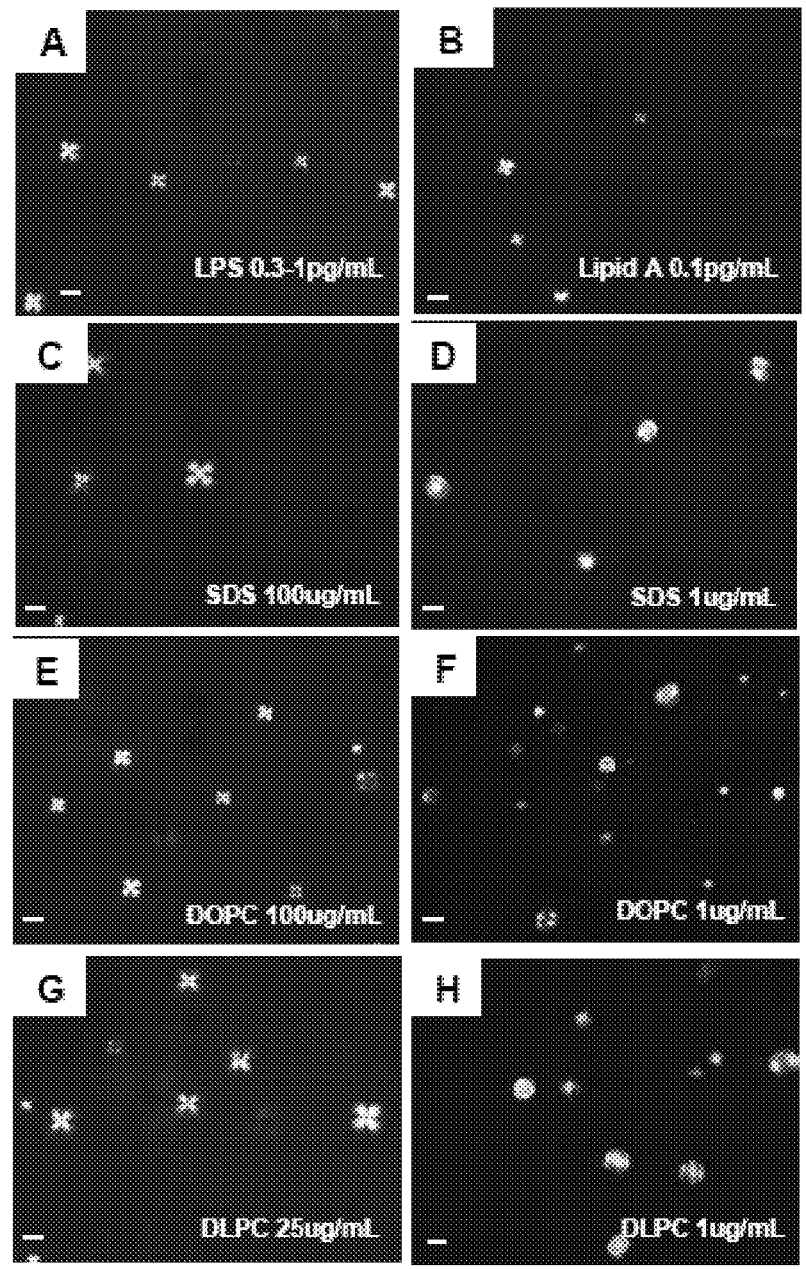
FIG. 9 shows polarized light micrographs of the 5CB emulsions upon contact with LPS (A), Lipid A (B), SDS (C and D), DOPC (E and F), and DLPC (G and H) under various concentrations of interest in the PBS buffer (contains less than 2 pg/mL LPS as certificated by the supplier) at room temperature. The 0.3-1 pg/mL LPS concentration is measured by a kinetic turbidimetric LAL assay. The amounts of 5CB emulsion and analyte solutions of interest are fixed as 0.4 μL, and 40 μL, over the measurements. Scale bars correspond to 5 μm.

To further test if the LC emulsion anchoring transition is specific to the LPS analyte, the inventors again contacted the LC emulsion droplets with Lipid A (diphosphoryl from E. Coli F583, a component of LPS), surfactant SDS, and the phospholipids DLPC and DOPC at various concentrations of interest (FIG. 9). For each of these tests, 0.4 uL emulsion and 40 uL test solution were used.

As shown by the appearance of isogyres in the polarized micrographs of FIG. 9, bipolar to radial anchoring transition of the LC emulsion droplets at pg/mL analyte concentration was observed upon contact only with intact LPS or Lipid A. In contrast, the bipolar to radial anchoring transition of the LC emulsion droplets upon contact with the surfactant SDS or the phospholipids DLPC and DOPC was observed only at the much higher µg/mL-100 µg/mL concentration range, and not at pg/mL concentrations.

Thus, the inventors have demonstrated that the high sensitivity of the method is specific to the detection of LPS and its components, leading to the conclusion that the highly sensitive and specific response of the LC droplets to endotoxin is caused by the unique structure of lipid A.

Example 6

Using Flow Cytometry in Detection and Quantification

This example demonstrates the feasibility of using a flow cytometer (light scattering mode) as a detector to distinguish between and quantify LC droplets in radial and bipolar configurations. Droplets having radial and bipolar anchoring configurations were passed through a flow cytometer. The results are shown in FIG. 10, which shows side light scattering intensity (SSC-H) plotted as a function of forward light scattering (FSC-H) intensity for LC droplets showing the bipolar configuration (FIG. 10A) and the radial configuration (FIG. 11B).

Figure 10:
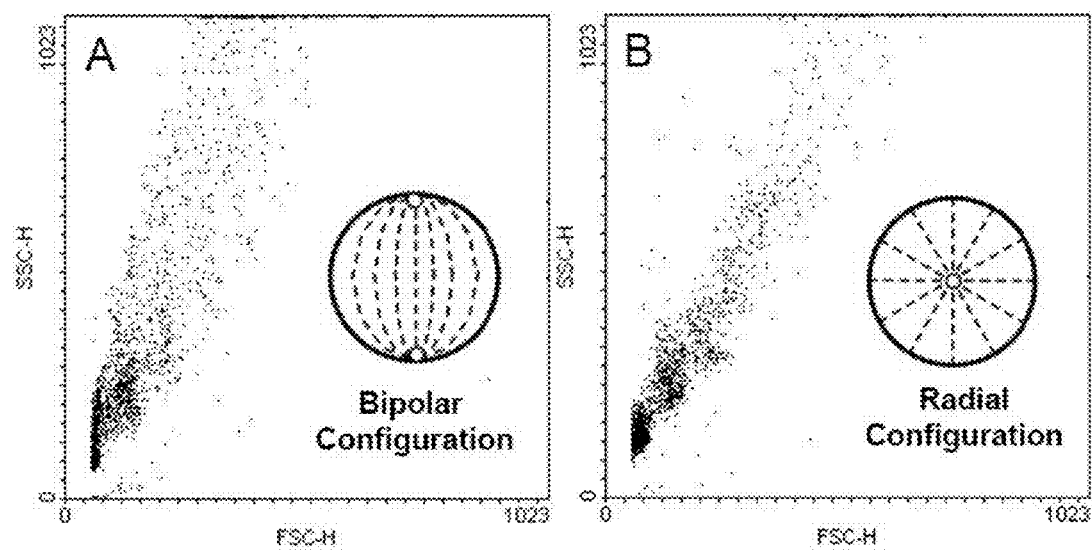
FIG. 10 are plots of flow cytometry measurements of LC droplets having bipolar anchoring configurations (11A) and radial anchoring configurations (11B). The intensity of side light scattering (SSC-H) is plotted as a function of forward light scattering (FSC-H).

Inspection of FIG. 10 reveals that the ratio of side-scattering to forward scattering of light is dependent on the internal configuration of the LC droplets. In addition, the tighter distribution of the data in FIG. 10B is consistent with the higher degree of symmetry present in the LC droplets with the radial configuration (the scattering of light from radial droplet is invariant to rotation of the droplet; scattering from bipolar droplets depends on the orientations of the droplets and the incident light). This result suggests a potentially rapid and high throughput methodology to quantify the relative populations of radial and bipolar LC droplets, and thus to detect and quantify LPS using the method of the present invention.

Example 7

LPS Interaction with Point Defects in the LC: a Proposed Mechanism of Specificity The inventors calculated that if all the LPS endotoxin in 40 µL of a 1 pg/ml solution adsorbed uniformly over the aqueous-LC interface of 1,500 LC droplets (radius 3 µm) dispersed in an aqueous solution, the surface density of endotoxin molecules would be ~350,000 nm$^2$/molecule or ~$10^{-5}$ of saturation monolayer coverage (~$10^{-5}$ Langmuir). In contrast, double-tailed lipids such as DLPC and DOPC trigger ordering transitions at interfacial concentrations that correspond to 0.6 nm$^2$/molecule (saturation coverage is ~0.4 nm$^2$/molecule). This large difference in surface density (5-to-6 orders of magnitude) that is required to trigger the ordering transition within the LC droplet suggests that LPS endotoxin triggers the anchoring configuration transition through interaction with a localized region of the LC droplet, such as a defect, and not through uniform surface adsorption, as has been established for lipids such as DLPC.

To test this hypothesis, the inventors changed the geometry of the system (the presence of topological defects is strongly dependent on geometry). Specifically, the inventors measured the ordering transition induced by endotoxin at planar interfaces. In contrast to the LC droplets, neither lipid A nor endotoxin reordered micrometer-thick films of nematic 5CB (with planar interfaces) until the concentration of lipid A or endotoxin exceeded mg/mL (see also Example 2). Furthermore, the inventors transferred Langmuir monolayers of lipid A onto the planar interfaces of nematic films of 5CB, and determined that a surface concentration of lipid A of ~1.15 nm²/molecule was required to cause an ordering in the LC that resulted in a perpendicular orientation.

Given that lipid A has 6 tails whereas conventional phospholipids such as DLPC have two, at planar interfaces, lipid A triggers an ordering transition in the LC at an interfacial density of lipid tails that is comparable to DLPC. That is, at planar interfaces, lipid A drives the ordering transition in the LC through a uniform adsorption at the interface of the LC. This result strongly supports the hypothesis that the endotoxin triggers the anchoring configuration transition reported in micrometer-sized LC droplets through geometry-dependent defects.

Figure 11A:
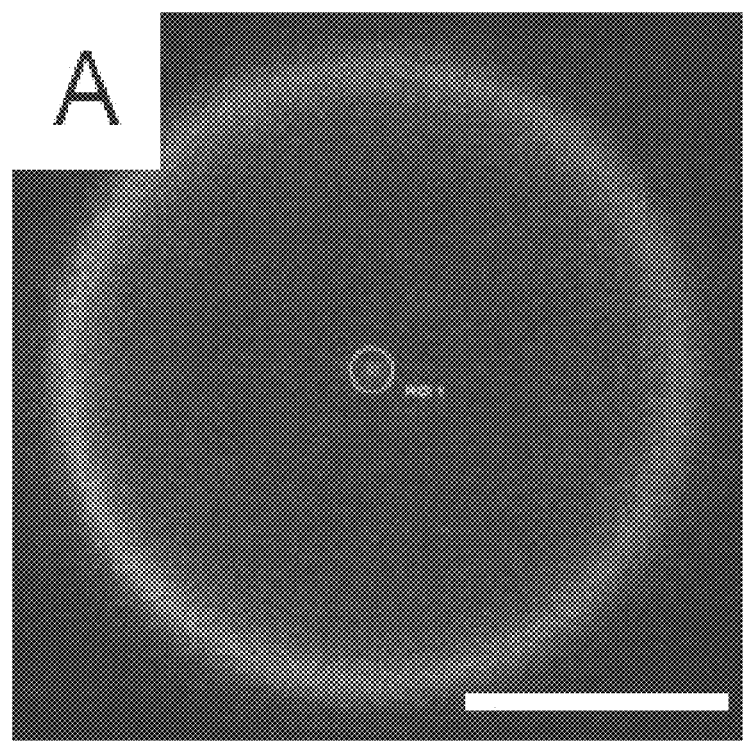
FIG. 11A is a confocal fluorescent micrographs of a BODIPY FL-endotoxin-decorated LC droplet (contacted with a 20 µg/ml BODIPY FL-endotoxin) having radial configuration. The region of interest (ROI) for photobleaching measurements is within the smaller white circle.
Figure 11B:
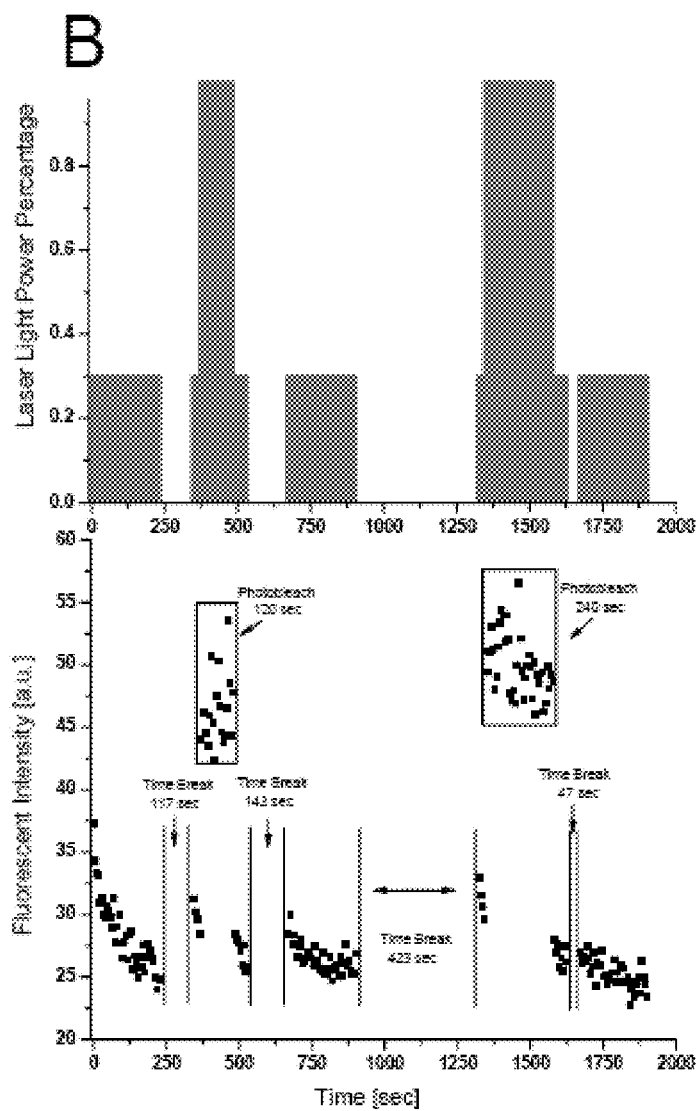
FIG. 11B is a plot of fluorescent intensity observed (bottom) and laser light power used (top) during photobleaching of the ROI shown in FIG. 13A as a function of time. During the photobleaching progress, 30% laser light power was used for time series measurement and 100% laser light power for the intended photobleaching. Scale bar is 5 µm.

To provide insight into the interactions of endotoxin with the defects of the LC microdroplets, the inventors performed confocal microscopy using BODIPY-labeled endotoxin. The confocal microscope measurements were performed with 100 μL of 20 μg/mL BODIPY FL-ENDOTOXIN with ~21,500 LC droplets in a PBS solution. These measurements confirmed that endotoxin was concentrated at a point defect formed at the center of the LC droplets with a radial configuration (see FIG. 11A).

Furthermore, following deliberate photobleaching of the BODIPY-labeled endotoxin within the point defect at the center of the droplet, the inventors measured recovery of the fluorescence (see FIG. 11B), with the results indicating an exchange of LPS endotoxin between the point defect and surface of the droplet occurred on a time-scale of seconds. For the time series and photobleaching measurements of LC droplets, the inventors selectively chose the BODIPY FL-ENDOTOXIN-decorated LC droplets adsorbed at the bottom cover slip substrate due to the inability to trace the mobile LC droplets; corresponding LC anchoring was confirmed under bright field microscope measurement.

Figure 11C:
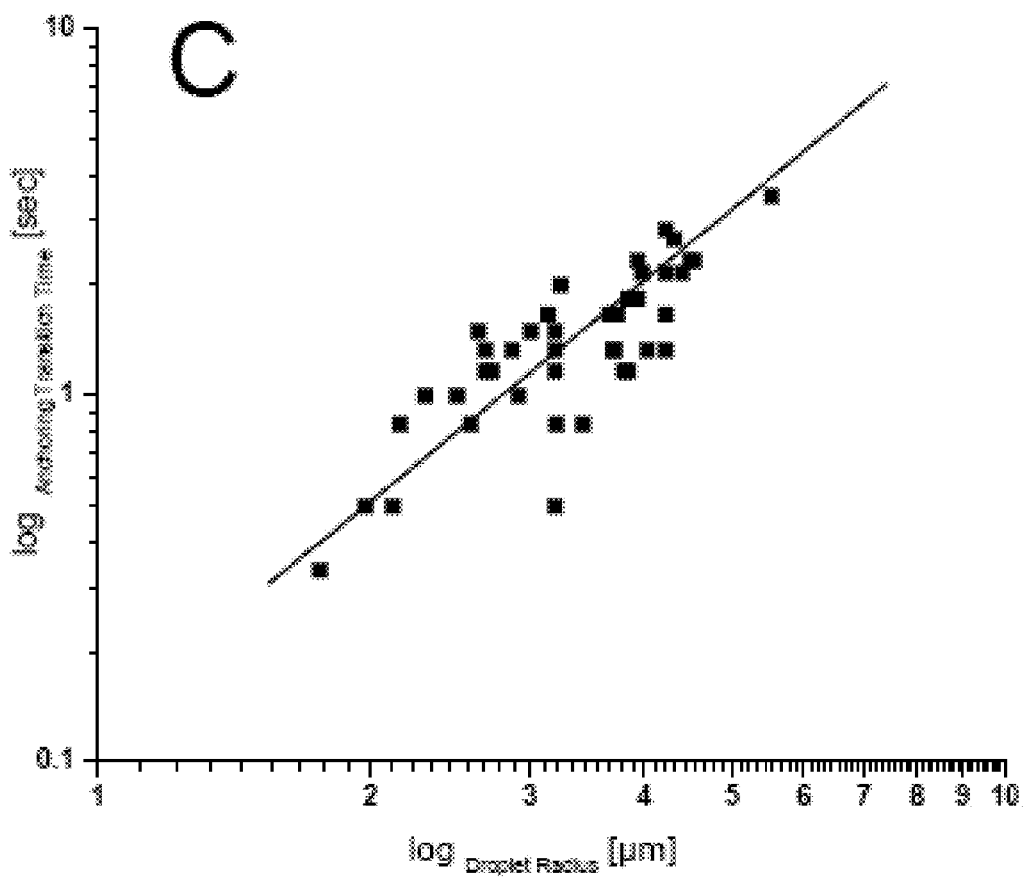
FIG. 11C is a plot of time interval of bipolar-to-radial anchoring configuration transition versus LC droplet radii in a thermal quenching experiment. The volume of the 10 pg/mL endotoxin solution was 100 µL and the number of LC droplets in the endotoxin solution was 21,500. The measurements were performed by imaging the LC bipolar-to-radial anchoring transition upon LC transition as the LC droplet moved freely in the bulk solution.

The inventors hypothesized that the ordering transition driven by a surface concentration of endotoxin of ~$10^{-5}$ Langmuir that results in the central point defect would require transport of the adsorbed endotoxin across the interface of the droplet to the Boojum defects. To test this hypothesis, an emulsion of 5CB was heated above the clearing temperature of the nematic phase ($T_{iso}$=33.5°; experiments were performed at 50° C.), and added to a 10 pg/mL solution of endotoxin also heated to 50° C. Upon cooling, the time interval between the first appearance of the nematic phase and the establishment of radial ordering within the LC droplet was measured. As shown in FIG. 11C, the time interval required for the droplets to exhibit radial ordering (following appearance of the nematic phase) increases with the size of the droplet when the endotoxin concentration was 10 pg/ml. These results are consistent with a diffusive process, in which the response time scales with the square of a characteristic diffusion length.

The inventors calculated the time for lateral diffusion of lipid to a localized region on the droplet surface following the quench into the nematic phase ($t_1 = L_A^2/4D_s$ where $L_A$ corresponds to πR/2 the distance along the surface from the equator to the pole regions) to be ~0.6 s (using Ds~$10 \times 10^{-12}$ m²/s) for the droplets with a diameters of 6 μm. This result suggests that lateral diffusion of endotoxin across the droplet surface determines the dynamics of the ordering transition, thus providing additional support for the idea that the ordering transitions of the LC droplets occur via localized interactions of the endotoxin.

The results suggest that endotoxin triggers the ordering transition in the micrometer-sized LC droplets through interaction with the defects of the droplets and not through changes in surface anchoring of the LC. Because the inventors' measurements with Langmuir-Shaefer films of lipid A indicate that $10^{-5}$ L of lipid A has no measurable effect on surface anchoring, the inventors conclude that the lipid A-induced ordering transition of the LC droplets from the bipolar to radial configuration leads to an increase in surface energy of the droplets $E_{surface}$~$WR^2$. If the elastic strain of the LC within the droplet is described by a single elastic constant, the transition from the bipolar to radial configuration does not result in a change in the magnitude of the elastic energy stored in the strained states of the droplets ($E_{elastic}$~KR, where K is the elastic constant).

The transition from the bipolar to radial configuration results in a decrease in the number of point defects in the system from two (two Boojums) to one (radial). If one assumes the energy of the core of the Boojum and central point defects are similar in magnitude, the bipolar to radial ordering transition is accompanied by a decrease in energy of $E_{core}$~$4\pi/3 r_c^3 \in_c$, where $r_c$ is the radius of the core of the defect and $\in_c$ is the melting energy density. The size of the core can be estimated by the competing effects of the elastic energy density and melting density as $r_c$~$(K/\in_c)^{0.5}$, thus resulting in $E_{core}$~$4\pi/3 \in_c^{-0.5} K^{1.5}$.

This model suggests that defect-driven ordering transitions can occur when $E_{core} > E_{surface}$, or $R < (E_{core}/W)^{0.5}$. By approximating $\in_c$ as the enthalpy of the nematic to isotropic transition (~$10^6$ J/m³), W as $10^{-4}$ J/m² and K as $10^{-11}$N, the inventors calculated that the ordering of the droplets will be strongly influenced by defects energies for R<11 μm. Indeed, the inventors' observation that endotoxin does not trigger ordering transitions in droplets substantially greater than 10 μm in size in the pg/ml range is consistent with the above proposed model for defect-driven ordering transitions.

Although the invention is not limited by any particular theory or proposed mechanism of action, the inventors' discovery of this new proposed mechanism for the method's surprising sensitivity and specificity to LPS provides a further illustration of the novelty of the claimed devices and methods.

Example 8

LPS Sensor Using LC Microdomains Immobilized in a Gel

Figure 12:
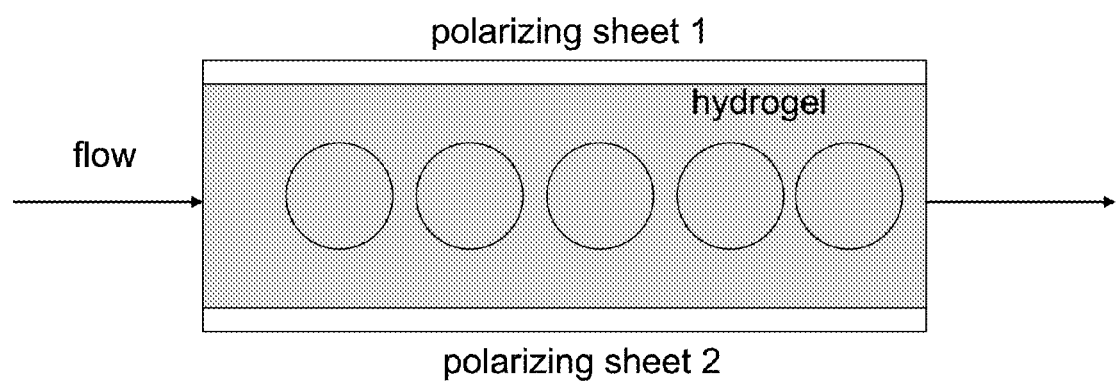
FIG. 12 is a schematic illustration of LC droplets hosted in a hydrogel, through which an LPS-containing sample is flowed.

In this prophetic example, the inventors explain how a hydrogel could be used in an LPS sensor to keep the LC droplets dispersed. FIG. 12 shows a device containing LC droplets hosted in a hydrogel, through which an LPS-containing test sample is flowed. Visual inspection of the array of droplets could be used to report the presence of LPS. Such a design could be employed in a lateral flow device (similar to a pregnancy test) that integrates the LC-droplet-based detection of LPS. The LC droplets may be immobilized in hydrogels. Notably, polymeric materials that can be used to create hydrogels do not trigger an optical response in LC droplets. Hydrogel may be formed via photo or chemical cross-linking about dispersion of LC droplets. Other possible approaches include impregnating a hydrogel gel with an isotropic mixture of a volatile solvent and a LC-forming compound. Upon evaporation of the volatile solvent, the mesogen will phase separate to form LC droplets within the gel. This procedure is known in the art and has been used to prepare dispersions of LC droplets in polymeric networks used in LC displays.

In one embodiment of this approach, the hydrogel is dehydrated, and hydration of the hydrogel is used to draw the aqueous sample containing endotoxin into contact with the LC droplets. In a second embodiment, the hydrogel is hydrated prior to introduction of the sample, and an absorbent material is placed downstream of the hydrogel in order to draw the sample across the LC droplets using capillary forces. These embodiments represent the essential principles of lateral flow devices that have been successful as the basis of diagnostics suitable for use in low-resource environments.

Example 9

Figure 13:
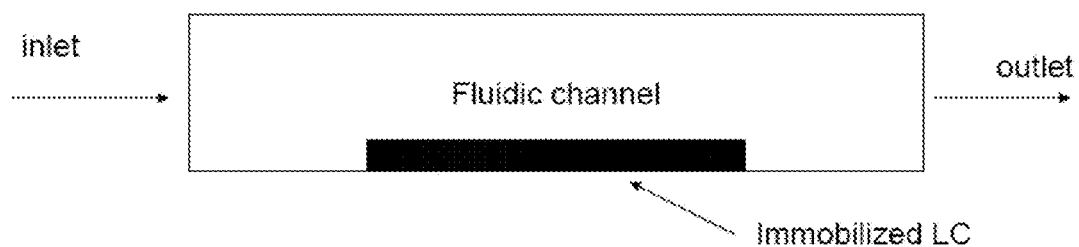
FIG. 13 is a schematic illustration of LC droplets immobilized on a surface within a microfluidic channel.

LC Sensor for LPS Based on Microdomains of LC Supported on a Surface and Exposed to a Sample Using a Microfluidic Channel In this prophetic example of the invention, LC droplets of 5CB with diameters of 50 micrometers are dispensed using a piezodispenser onto a glass slide treated with octadecyltrichlorosilane. A PDMS microchannel is layered over the supported droplets, and an aqueous sample containing LPS is passed through the channel. The optical appearance of the supported LC droplets are monitored using a polarized light microscope. A change in optical appearance of the droplets is observed when LPS adsorbs to the interface of the droplets, thus denoting the presence of the LPS in the sample. A more generalized illustration of this Example, wherein a sample passes through a fluidic channel, contacting immobilized LC microdomains in the process, is shown in FIG. 13.

Example 10

LC Sensor Based on Microdomains of LC Formed within a Colloid-in-LC Gel

Figure 16:
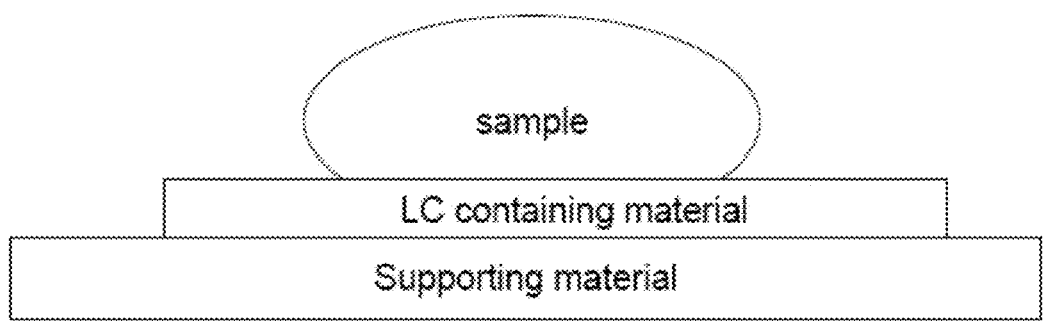
FIG. 16 is a schematic illustration of an embodiment of the invention in which a droplet of a sample is placed onto an LC containing material that is supported on a solid surface.

In this prophetic example of the invention, 1 micrometer-sized polystyrene spheres are dispersed in the isotropic phase of 5CB, and then placed onto a warmed microscope slide treated with octadecyltrichlorosilane. A 5 micrometer thick film of the isotropic 5CB and microspheres is formed on the slide, and then cooling into the nematic phase of 5CB to form a thin gel comprised of micrometer-sized LC domains. A droplet of an aqueous solution containing LPS is placed into contact with the free surfaces of the micrometer-sized domains, and the optical appearance of the domains is determined using a polarized light microscope in transmission mode. The presence of LPS with the sample is reported as a change in the optical appearance of the domains. A more generalized illustration of this Example, wherein a sample applied on top of an LC-containing material that is itself placed on top of a separate supporting material, is shown in FIG. 16.

Example 11

Calibration Curve and Volume Measurement of LC in LC Emulsion

In this example, the inventors quantified the volume of 5CB contained within 0.4 µL droplets of 5CB emulsion prepared as outlined in Example 1.

Figure 17:
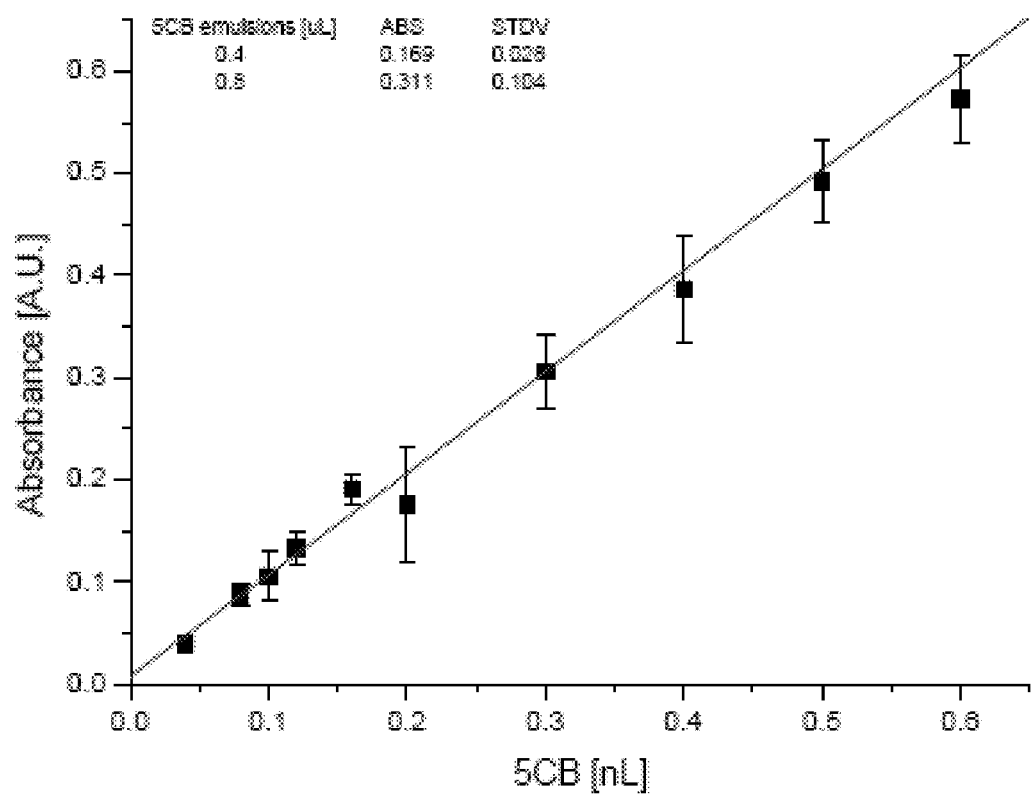
FIG. 17 is an absorbance calibration curve plotting absorbance at a wavelength of ~280 nm (X axis) as a function of known volumes 5CB (Y axis, volume 5CB in nL).

Various known volumes of 5CB were dissolved into 1 mL ethanol solution. UV-Vis absorbance spectroscopy measurements at an absorbance peak wavelength of ~280 nm were performed on the standardized samples. A calibration curve plotting known 5CB volume as a function of absorbance was produced (FIG. 17). To ensure that no additional absorbance peak is observed for PBS buffer under the UV-Vis scan wavelength, additional absorbance measurements were performed for a solution of 10 µL PBS buffer in 1 mL ethanol.

5CB emulsions were prepared as previously reported in Example 1 (2 µL 5CB in 1 mL PBS buffer). 0.44, of the resulting 5CB emulsion was mixed into 1 mL ethanol, and UV-Vis measurement preformed. The inventors then used the calibration curve (FIG. 17) to quantify the 5CB volume in both a 0.4 µL and 0.8 µL drop of the 5CB emulsion. As the calibration curve shows, 5CB volume vs. absorbance intensity is a linear relationship. The 0.4 µL and 0.8 µL (two separated 0.4 µL, droplets added) 5CB emulsions contained 0.16 nL and 0.32 nL 5CB, respectively, indicating a ratio of liquid crystal volume to emulsion volume of 0.0004/1. These results were reproduced over the several samples tested.

Those skilled in the art will recognize, or be able to ascertain using no more than routine experimentation, numerous equivalents to the specific materials and methods described herein. Such equivalents are considered to be within the scope of this invention and encompassed by the following claims.

We claim:

1. A liquid crystal-based sensor system for detecting an analyte in a test sample having an analyte concentration of less than 1 µg/ml, comprising:
   (a) one or more liquid crystal microdomains that are confined by an interface that generates one or more point defects in the liquid crystal microdomains, wherein the liquid crystal microdomains are dispersed and have a minor axis of between about 0.5 µm and about 200 µm;
   (b) a detector capable of characterizing the orientational order of the liquid crystal microdomains, and
   (c) a test sample comprising an analyte having a concentration of less than 1 µg/ml in contact with the microdomains;
   wherein at least one of the liquid crystal microdomains has one point defect.

2. The liquid crystal-based sensor of claim 1, wherein the microdomains are confined within droplets, within microwells, within capillaries, on surfaces, or within another material.

3. The liquid crystal-based sensor of claim 1 wherein the microdomains have curved interfaces.

4. The liquid crystal-based sensor of claim 2, wherein the liquid crystal microdomains are dispersed liquid crystal droplets within a liquid crystal emulsion.

5. The liquid crystal-based sensor of claim 1, wherein the detector capable of characterizing the orientational order of the liquid crystal microdomains characterizes the orientational order by determining the number of point defects in the liquid crystal microdomains, detecting the anchoring configuration of said microdomains, or both.

6. The liquid crystal-based sensor of claim 1, wherein the detector uses light-based detection.

7. The liquid crystal-based sensor of claim 6, wherein the detector is a light-based imaging device.

8. The liquid crystal-based sensor of claim 1, wherein the detector is located on a flow device.

9. The liquid crystal-based sensor of claim 1, wherein a plurality of liquid crystal microdomains are dispersed within a material that is supported on a solid support.

10. The liquid crystal-based sensor of claim 4, wherein the liquid crystal emulsion further comprises an LPS free aqueous phase.

11. The liquid crystal-based sensor of claim 4, wherein the test sample is an aqueous test sample in contact with the liquid crystal emulsion.

12. The liquid crystal-based sensor of claim 11, wherein the volume ratio of the aqueous test sample to the liquid crystal contained within the liquid crystal emulsion is greater than or equal to about 100 to 1.

13. The liquid crystal-based sensor of claim 1, wherein at least another one of the liquid crystal microdomains have two point defects.

14. The liquid crystal-based sensor of claim 1, wherein the analyte is endotoxin lipopolysaccharide (LPS) or lipid A.

15. The liquid crystal-based sensor of claim 1, wherein the liquid crystal microdomains are immobilized.

16. The liquid crystal-based sensor of claim 1, wherein the liquid crystal within the microdomains is 4'-pentyl-4-cyanobiphenyl (5CB).

17. A method for detecting an analyte in a test sample having an analyte concentration of less than 1 µg/ml, comprising the steps of:
   (a) providing one or more liquid crystal microdomains having one point defects, wherein the liquid crystal microdomains have a minor axis of between about 0.5 µm and about 200 µm;
   (b) contacting the microdomains with a test sample having an analyte concentration of less than 1 µg/ml; and
   (c) using a detector to determine the number of point defects in the liquid crystal microdomains, wherein a change in the number of point defects indicates the presence of the analyte in the test sample.

18. The method of claim 17, wherein the interface of the liquid crystal microdomain is curved.

19. The method of claim 17, wherein the change in the number of point defects in the liquid crystal microdomains is a reduction in the number of point defects within the microdomains.

20. The method of claim 17, wherein the number of point defects in the liquid crystal microdomains is determined by detecting the anchoring configuration of the microdomains.

21. The method of claim 17, wherein the test sample is an aqueous test sample.

22. The method of claim 17, wherein the analyte is endotoxin lipopolysaccharide (LPS) or lipid A.

23. The method of claim 20, wherein the step of using a detector to detect any change in configuration of the liquid crystal microdomains is performed by one or more of the group consisting of optical imaging, fluorescence imaging, optical imaging using polarized light, polarized light microscopy, bright field microscopy, fluorescence microscopy, light scattering measurement, flow cytometry, fluorescence flow cytometry, microelectrophoresis, dielectrophoresis, measurement of electrical capacitance, measurement of magnetic properties, measuring turbidity, detecting optical reflection, detecting transmittance of light, visual inspection, using a plate reader, using microwell plates, and using a cuvette in a detector.

24. The method of claim 17, further comprising the step of using a microfluidic device to deliver the sample to the detector.

25. The method of claim 17, wherein a plurality of dispersed liquid crystal microdomains are provided.

26. The method of claim 25, further comprising the step of using the liquid crystal defect information for the dispersed microdomains to quantify the analyte present in the sample.

27. The method of claim 26, wherein the analyte is endotoxin lipopolysaccharide (LPS) or lipid A.

28. The method of claim 25, wherein the step of providing a plurality of dispersed liquid crystal microdomains comprises providing a liquid crystal in water emulsion wherein the liquid crystal microdomains are liquid crystal droplets.

29. The method of claim 28, wherein the test sample is an aqueous test sample, and the volume ratio of the aqueous test sample to the liquid crystal contained within the liquid crystal emulsion is greater than or equal to about 100 to 1.

30. A method of making a liquid crystal-based sensor system for detecting an analyte in a test sample having an analyte concentration of less than 1 µg/ml, the method comprising the steps of:
   (a) providing a material comprising dispersed liquid crystal microdomains having one point defects and having a minor axis of between about 0.5 µm and about 200 µm;
   (b) providing a detector capable of detecting the anchoring configuration of the liquid crystal microdomains; and
   (c) contacting a test sample comprising an analyte having a concentration of less than 1 µg/ml with the microdomains.

31. The method of claim 30, wherein the step of providing the material comprising dispersed liquid crystal microdomains further comprises immobilizing the dispersed liquid crystal microdomains onto a substrate surface.

32. A liquid crystal-based sensor system for detecting endotoxin lipopolysaccharide (LPS) in a test sample having an LPS concentration of less than 1 µg/ml, comprising:
   (a) a material containing dispersed liquid crystal microdomains having one point defect and having a minor axis of between about 0.5 µm and about 200 µm;
   (b) a detector capable of detecting the anchoring configuration of the liquid crystal microdomains; and
   (c) a test sample comprising LPS at a concentration of less than 1 µg/ml in contact with the microdomains.

33. A method for detecting endotoxin lipopolysaccharide (LPS) in a test sample having an LPS concentration of less than 1 µg/ml, comprising the steps of:
   (a) providing a material comprising dispersed liquid crystal microdomains having one point defect and having a minor axis of between about 0.5 µm and about 200 µm;
   (b) contacting the material with an aqueous test sample comprising LPS at a concentration of less than 1 µg/ml; and
   (c) using a detector to detect the anchoring configuration of the liquid crystal microdomains.

* * * * *